(12) United States Patent
Imhof-Jung et al.

(10) Patent No.: US 9,676,845 B2
(45) Date of Patent: *Jun. 13, 2017

(54) BISPECIFIC ANTIGEN BINDING PROTEINS

(75) Inventors: Sabine Imhof-Jung, Planegg (DE);
Christian Klein, Bonstetten (CH);
Joerg Thomas Regula, Munich (DE);
Wolfgang Schaefer, Mannheim (DE);
Juergen Michael Schanzer, Traunstein (DE)

(73) Assignee: Hoffmann-La Roche, Inc., Nutley, NJ (US)

( * ) Notice: Subject to any disclaimer, the term of this patent is extended or adjusted under 35 U.S.C. 154(b) by 1024 days.

This patent is subject to a terminal disclaimer.

(21) Appl. No.: 12/780,971

(22) Filed: May 17, 2010

(65) Prior Publication Data

US 2010/0316645 A1  Dec. 16, 2010

(30) Foreign Application Priority Data

Jun. 16, 2009 (EP) ..................... 09007857

(51) Int. Cl.
*A61K 39/395* (2006.01)
*C07K 16/22* (2006.01)
*C07K 16/46* (2006.01)

(52) U.S. Cl.
CPC ............ *C07K 16/22* (2013.01); *C07K 16/468* (2013.01); *C07K 2317/31* (2013.01); *C07K 2317/35* (2013.01); *C07K 2317/55* (2013.01); *C07K 2317/56* (2013.01); *C07K 2317/64* (2013.01); *C07K 2317/66* (2013.01); *C07K 2317/73* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,150,149 A | 4/1979 | Wolfsen et al. | |
| 4,361,544 A | 11/1982 | Goldenberg | |
| 4,444,744 A | 4/1984 | Goldenberg | |
| 4,737,456 A | 4/1988 | Weng et al. | |
| 5,202,238 A | 4/1993 | Fell et al. | |
| 5,204,244 A | 4/1993 | Fell et al. | |
| 5,571,894 A | 11/1996 | Wels et al. | |
| 5,587,458 A | 12/1996 | King et al. | |
| 5,624,821 A | 4/1997 | Winter et al. | |
| 5,677,425 A | 10/1997 | Bodmer et al. | |
| 5,731,168 A | 3/1998 | Carter et al. | |
| 5,747,654 A | 5/1998 | Pastan et al. | |
| 5,789,199 A | 8/1998 | Joly et al. | |
| 5,798,229 A | 8/1998 | Strittmatter et al. | |
| 5,821,333 A | 10/1998 | Carter et al. | |
| 5,840,523 A | 11/1998 | Simmons et al. | |
| 5,869,046 A | 2/1999 | Presta et al. | |
| 5,959,083 A | 9/1999 | Bosslet et al. | |
| 5,959,177 A | 9/1999 | Hein et al. | |
| 6,040,498 A | 3/2000 | Stomp et al. | |
| 6,166,185 A | 12/2000 | Davis et al. | |
| 6,171,586 B1 | 1/2001 | Lam et al. | |
| 6,194,551 B1 | 2/2001 | Idusogie et al. | |
| 6,239,259 B1 | 5/2001 | Davis et al. | |
| 6,248,516 B1 | 6/2001 | Winter et al. | |
| 6,267,958 B1 | 7/2001 | Andya et al. | |
| 6,417,429 B1 | 7/2002 | Hein et al. | |
| 6,420,548 B1 | 7/2002 | Vezina et al. | |
| 6,511,663 B1 | 1/2003 | King et al. | |
| 6,558,672 B1 | 5/2003 | Pastan et al. | |
| 6,586,207 B2 | 7/2003 | Tirrell et al. | |
| 6,602,684 B1 | 8/2003 | Umana et al. | |
| 6,897,044 B1 | 5/2005 | Braslawsky et al. | |
| 6,946,292 B2 | 9/2005 | Kanda et al. | |
| 6,982,321 B2 | 1/2006 | Winter | |
| 7,125,978 B1 | 10/2006 | Vezina et al. | |
| 7,129,330 B1 | 10/2006 | Little et al. | |
| 7,276,585 B2 | 10/2007 | Lazar et al. | |
| 7,317,091 B2 | 1/2008 | Lazar et al. | |
| 7,355,008 B2 | 4/2008 | Stavenhagen et al. | |
| 7,381,408 B2 | 6/2008 | Mezo et al. | |
| 7,642,228 B2 | 1/2010 | Carter et al. | |
| 7,651,688 B2 | 1/2010 | Hanai et al. | |
| 7,666,622 B2 | 2/2010 | Sharma et al. | |
| 7,695,936 B2 | 4/2010 | Carter et al. | |
| 7,919,257 B2 | 4/2011 | Hoogenboom et al. | |
| 7,942,042 B2 | 5/2011 | Kawakita et al. | |

(Continued)

FOREIGN PATENT DOCUMENTS

CN    1173878 A    2/1998
CN    1176659 A    3/1998

(Continued)

OTHER PUBLICATIONS

Chan, L.A., et al., Variable Region Domain Exchange in Human IgGs Promotes Antibody Complex Formation with Accompanying Structural Changes and Altered Effector Functions; Molecular Immunology, 41 (2004) 527-538 XP002519713.

Miller, K., et al., Design, Construction, and In Vitro Analyses of Multivalent Antibodies; Journal of Immunology, 170 (2003) 4854-4861 XP002508787.

Morrison, S.L., et al., Variable Region Domain Exchange Influences the Functional Properties of IgG; Journal of Immunology 160 (1998) 2802-2808 XP003001892.

Morrison, S.L., Two Heads Are Better Than One; Nature Biotechnology 25:11 (2007) 1233-1234.

(Continued)

*Primary Examiner* — Laura B Goddard
*Assistant Examiner* — Meera Natarajan
(74) *Attorney, Agent, or Firm* — Morrison & Foerster LLP

(57) ABSTRACT

The present invention relates to bispecific antigen binding proteins, methods for their production, pharmaceutical compositions containing said antibodies, and uses thereof.

8 Claims, 9 Drawing Sheets

(56) References Cited

U.S. PATENT DOCUMENTS

| | | |
|---|---|---|
| 8,188,231 B2 | 5/2012 | Lazar et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Junutula et al. |
| 8,796,424 B2 | 8/2014 | Croasdale et al. |
| 8,945,552 B2 | 2/2015 | Baehner et al. |
| 9,150,639 B2 | 10/2015 | Yamasaki et al. |
| 9,241,994 B2 | 1/2016 | Igawa |
| 2002/0062010 A1 | 5/2002 | Arathoon et al. |
| 2002/0155537 A1 | 10/2002 | Carter et al. |
| 2003/0099974 A1 | 5/2003 | Lillie et al. |
| 2003/0124129 A1 | 7/2003 | Oliner |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Mertens et al. |
| 2005/0054048 A1 | 3/2005 | Grasso et al. |
| 2005/0064509 A1 | 3/2005 | Bradbury et al. |
| 2005/0079170 A1 | 4/2005 | Le Gall et al. |
| 2005/0152894 A1 | 7/2005 | Krummen et al. |
| 2005/0163782 A1 | 7/2005 | Glaser et al. |
| 2005/0249722 A1 | 11/2005 | Beliard et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Mattheus Hoogenboom et al. |
| 2006/0280747 A1 | 12/2006 | Fuh et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0269369 A1 | 11/2007 | Gegg et al. |
| 2007/0274985 A1 | 11/2007 | Dubel et al. |
| 2007/0274998 A1 | 11/2007 | Utku |
| 2008/0063641 A1 | 3/2008 | Huang et al. |
| 2008/0187954 A1 | 8/2008 | Kallmeier et al. |
| 2009/0023811 A1 | 1/2009 | Biadatti et al. |
| 2009/0060910 A1 | 3/2009 | Johnson |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 8/2009 | Kobaru |
| 2009/0232811 A1 | 9/2009 | Klein et al. |
| 2010/0015133 A1 | 1/2010 | Igawa et al. |
| 2010/0081796 A1 | 4/2010 | Brinkman et al. |
| 2010/0111967 A1 | 5/2010 | Baechner et al. |
| 2010/0254989 A1 | 10/2010 | Bossenmaier et al. |
| 2010/0256338 A1 | 10/2010 | Brinkmann et al. |
| 2010/0256340 A1 | 10/2010 | Brinkmann et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0149879 A1 | 6/2012 | Brinkmann et al. |
| 2012/0164726 A1 | 6/2012 | Klein et al. |
| 2012/0177637 A1 | 7/2012 | Hoogenboom et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0112914 A1 | 4/2014 | Nezu et al. |
| 2014/0199294 A1 | 7/2014 | Mimoto et al. |
| 2014/0249296 A1 | 9/2014 | Ploegh |
| 2014/0294810 A1 | 10/2014 | Lowman et al. |
| 2014/0370019 A1 | 12/2014 | Bruenker et al. |
| 2014/0370020 A1 | 12/2014 | Kuramochi et al. |
| 2015/0232541 A1 | 8/2015 | Fenn |
| 2015/0232560 A1 | 8/2015 | Heindl et al. |
| 2015/0291704 A1 | 10/2015 | Beck |
| 2015/0344570 A1 | 12/2015 | Igawa et al. |
| 2016/0039937 A1 | 2/2016 | Yamasaki et al. |
| 2016/0075785 A1 | 3/2016 | Ast et al. |
| 2016/0168259 A1 | 6/2016 | Igawa |
| 2016/0238600 A1 | 8/2016 | Hoogenboom et al. |

FOREIGN PATENT DOCUMENTS

| | | |
|---|---|---|
| CN | 12302039 A | 10/1999 |
| CN | 1603345 A | 4/2005 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 307 434 B2 | 3/1989 |
| EP | 0 637 593 A1 | 2/1995 |
| EP | 1 870 458 A1 | 12/2007 |
| EP | 1870459 | 12/2007 |
| EP | 1 925 319 A1 | 5/2008 |
| EP | 2 050 764 A1 | 4/2009 |
| EP | 2 443 154 B1 | 4/2012 |
| EP | 2 554 669 A1 | 2/2013 |
| EP | 2 647 707 A1 | 10/2013 |
| EP | 2 728 002 A1 | 5/2014 |
| EP | 2 787 078 A1 | 10/2014 |
| EP | 2 940 135 A1 | 10/2014 |
| JP | 2008-531049 A | 8/2008 |
| RU | 2005/123481 A | 1/2006 |
| RU | 2005/124281 A | 1/2006 |
| RU | 2295537 C2 | 3/2007 |
| WO | WO-93/01161 A1 | 1/1993 |
| WO | 93/06217 | 4/1993 |
| WO | WO-98/48032 A3 | 7/1993 |
| WO | WO-93/16185 A2 | 8/1993 |
| WO | WO-93/16185 A3 | 8/1993 |
| WO | WO-94/09131 A1 | 4/1994 |
| WO | 94/10202 | 5/1994 |
| WO | WO-94/29350 A2 | 12/1994 |
| WO | WO-94/29350 A3 | 12/1994 |
| WO | 95/09917 | 4/1995 |
| WO | 96/27011 | 9/1996 |
| WO | WO-96/26712 A1 | 9/1996 |
| WO | WO-96/27612 A1 | 9/1996 |
| WO | 97/01580 | 1/1997 |
| WO | WO-97/14719 A1 | 4/1997 |
| WO | WO-97/28267 A1 | 8/1997 |
| WO | WO-97/28267 C1 | 8/1997 |
| WO | 98/45331 | 10/1998 |
| WO | 98/45332 | 10/1998 |
| WO | WO-98/48032 A2 | 10/1998 |
| WO | WO-98/50431 A2 | 11/1998 |
| WO | 99/37791 | 7/1999 |
| WO | WO-99/54342 A1 | 10/1999 |
| WO | WO/99/66951 | * 12/1999 |
| WO | WO-00/05265 A2 | 2/2000 |
| WO | 00/35956 | 6/2000 |
| WO | WO-00/61739 A1 | 10/2000 |
| WO | 01/77342 | 10/2001 |
| WO | WO-01/90192 A2 | 11/2001 |
| WO | WO-02/02781 A1 | 1/2002 |
| WO | WO-02/33073 A1 | 4/2002 |
| WO | WO-02/096948 A2 | 12/2002 |
| WO | 03/030833 | 4/2003 |
| WO | WO-03/035835 A2 | 5/2003 |
| WO | WO-03/035835 A3 | 5/2003 |
| WO | 03/057134 | 7/2003 |
| WO | WO-03/055993 A1 | 7/2003 |
| WO | WO-03/073238 A2 | 9/2003 |
| WO | WO-03/073238 A3 | 9/2003 |
| WO | WO-03/097105 A1 | 11/2003 |
| WO | 03/106501 | 12/2003 |

(56) References Cited

FOREIGN PATENT DOCUMENTS

| WO | WO-2004/003019 A2 | 1/2004 |
|---|---|---|
| WO | WO-2004/003019 A3 | 1/2004 |
| WO | WO-2004/032961 A1 | 4/2004 |
| WO | WO-2004/058298 A1 | 7/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO-2004/106375 A1 | 12/2004 |
| WO | 2005/000900 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035727 A2 | 4/2005 |
| WO | WO-2005/035727 A3 | 4/2005 |
| WO | 2005/044853 | 5/2005 |
| WO | WO-2005/044859 A2 | 5/2005 |
| WO | WO-2005/044859 A3 | 5/2005 |
| WO | WO-2005/051422 A1 | 6/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/092925 A2 | 10/2005 |
| WO | WO 2005/092925 A3 | 10/2005 |
| WO | 2006/020258 | 2/2006 |
| WO | 2006/031370 | 3/2006 |
| WO | WO-2006/034488 A2 | 3/2006 |
| WO | WO-2006/034488 A3 | 3/2006 |
| WO | 2006/044908 | 4/2006 |
| WO | 2006/045049 | 4/2006 |
| WO | 2006/068953 | 6/2006 |
| WO | WO-2006/082515 A2 | 8/2006 |
| WO | WO-2006/082515 A3 | 8/2006 |
| WO | WO-2006/091209 A2 | 8/2006 |
| WO | WO-2006/091209 A3 | 8/2006 |
| WO | 2006/093794 | 9/2006 |
| WO | WO 2006/093794 * | 9/2006 |
| WO | WO-2006/093794 A1 | 9/2006 |
| WO | WO-2010/108127 A1 | 9/2006 |
| WO | WO-2006/103100 A2 | 10/2006 |
| WO | WO-2006/103100 A3 | 10/2006 |
| WO | WO-2006/106905 A1 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2006/132352 A1 | 12/2006 |
| WO | 2007/024715 | 3/2007 |
| WO | WO-2007/031875 A2 | 3/2007 |
| WO | WO-2007/031875 A3 | 3/2007 |
| WO | 2007/044887 | 4/2007 |
| WO | WO-2007/040837 A2 | 4/2007 |
| WO | WO-2007/048037 A2 | 4/2007 |
| WO | WO-2007/048037 A3 | 4/2007 |
| WO | 2007/068895 | 6/2007 |
| WO | WO-2007/084181 A2 | 7/2007 |
| WO | WO-2007/084181 A3 | 7/2007 |
| WO | WO-2007/095338 A2 | 8/2007 |
| WO | 2007/089445 | 9/2007 |
| WO | WO-2007/108013 A2 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/146959 A2 | 12/2007 |
| WO | WO-2007/146959 A3 | 12/2007 |
| WO | WO-2007/147901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/027236 A2 | 3/2008 |
| WO | WO-2008/027236 A3 | 3/2008 |
| WO | 2008/077077 | 6/2008 |
| WO | WO-2008/077546 A1 | 7/2008 |
| WO | WO-2008/100624 A2 | 8/2008 |
| WO | WO-2008/100624 A3 | 8/2008 |
| WO | 2008/132568 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO 2009/021754 A3 | 2/2009 |
| WO | WO-2009/023843 A1 | 2/2009 |
| WO | 2009/032782 | 3/2009 |
| WO | 2009/080251 | 7/2009 |
| WO | 2009/080252 | 7/2009 |
| WO | 2009/080253 | 7/2009 |
| WO | WO-2009/080254 A1 | 7/2009 |
| WO | WO-2009/089004 A1 | 7/2009 |
| WO | WO-2009/126944 A1 | 10/2009 |
| WO | WO-2010/034441 A1 | 4/2010 |
| WO | WO-2010/035012 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/087994 A2 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/118739 A1 | 9/2011 |
| WO | WO-2011/143545 A1 | 11/2011 |
| WO | WO-2012/025525 A1 | 3/2012 |
| WO | WO-2012/025530 A1 | 3/2012 |
| WO | WO-2012/058768 A1 | 5/2012 |
| WO | WO-2012/073985 A1 | 6/2012 |
| WO | WO-2012/116927 A1 | 9/2012 |
| WO | WO-2012/131555 A2 | 10/2012 |
| WO | WO-2012/131555 A3 | 10/2012 |
| WO | WO-2013/002362 A1 | 1/2013 |
| WO | WO-2013/003555 A1 | 1/2013 |
| WO | WO-2013/012733 A1 | 1/2013 |
| WO | WO-2013/026833 A1 | 2/2013 |
| WO | WO-2013/065708 A1 | 5/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/150043 A1 | 10/2013 |
| WO | WO-2013/157953 A1 | 10/2013 |
| WO | WO-2013/174873 A1 | 11/2013 |
| WO | WO-2014/081955 A1 | 5/2014 |
| WO | WO-2014/082179 A1 | 6/2014 |
| WO | WO-2014/104165 A1 | 7/2014 |
| WO | WO-2016/055432 A2 | 4/2016 |
| WO | WO-2016/055432 A3 | 4/2016 |

OTHER PUBLICATIONS

Rossi, E.A., et al., Multivalent Anti-CD20/Anti-CD22 Bispecific Antibody Fusion Proteins Made by the DNL Method Show Potent Lymphoma Cytotoxicity; Blood (ASH Annual Meeting Abstracts) 2006 108: Abstract 2495.

(56) References Cited

OTHER PUBLICATIONS

Simon, T., et al., Antibody Domain Mutants Demonstrate Autonomy of the Antigen Binding Site; The EMBO Journal 9:4 (1990) 1051-1056.
Atwell, S., et al., Stable Heterodimers from Remodeling the Domain Interface of a Homodimer Using a Phage Display Library; J. Mol. Biol. (1997) 270, 26-35.
Borgstrom, P., et al., Complete Inhibition of Angiogenesis and Growth of Microtumors by Anti-Vascular Endothelial Growth Factor Neutralizing Antibody: Novel Concepts of Angiostatic Therapy from Intravital Videomicroscopy; Cancer Research (1996) 56, 4032-4039.
Coloma, M.J., et al., Design and Production of Novel Tetravalent Bispecific Antibodies; Nature Biotechnology, vol. 15 (1997) 159-163.
Coxon, A., et al., Combined Treatment of Angiopoietin and VEGF Pathway Antagonists Enhances Antitumor Activity in Preclinical Models of Colon Carcinoma; 9th AACR Annual Meeting, Apr. 2008, Abstract #1113.
Fischer, N., et al., Bispecific Antibodies: Molecules That Enable Novel Therapeutic Strategies; Pathobiology (2007) 74: 3-14.
Holliger, P., et al., Engineered Antibody Fragments and the Rise of Single Domains; Nature Biotechnology, 23:9 (2005) 1126-1136.
Jendryko, N., et al., Simultaneous, Phenotypic Knockout of VEGF-R2 and Tie-2 With an Intradiabody Enhances Antiangiogenic Effects In Vivo; Therapieoptimierung and Risikostratifizierung, Scripps Research Institute, (2006) 218: 143-151.
Kim, K.J. et al., Inhibition of Vascular Endothelial Growth Factor-Induced Angiogenesis Suppresses Tumour Growth In Vivo; Nature, vol. 362 (1993) 841-844.
Liang, W.C., et al., Cross-species Vascular Endothelial Growth Factor (VEGF)-blocking Antibodies Completely Inhibit the Growth of Human Tumor Xenografts and Measure the Contribution of Stromal VEGF; Journal of Biological Chemistry, 281:2 (2006) 951-961.
Melnyk, O., et al., Vascular Endothelial Growth Factor Promotes Tumor Dissemination by a Mechanism Distinct from Its Effect on Primary Tumor Growth; Cancer Research, 56 (1996) 921-924.
Merchant, A.M., et al., An Efficient Route to Human Bispecific IgG; Nature Biotechnology, vol. 16 (1998) 677-681 XP002141015.
Morrison, S.L., et al., Chimeric Human Antibody Molecules: Mouse Antigen-Binding Domains with Human Constant Region Domains; Proc. Natl. Acad. Sci. USA, vol. 81 (1984) 6851-6855.
Oliner, J., et al., Suppression of Angiogenesis and Tumor Growth by Selective Inhibition of Angiopoietin-2; Cancer Cell (2004) vol. 6, 507-516.
Ridgway, J.B.B., et al., Knobs-into-Holes Engineering of Antibody CH3 Domains for Heavy Chain Heterodimerization; Protein Engineering, 9:7 (1996) 617-621.
Schoonjans, R., et al., Fab Chains as an Efficient Heterodimerization Scaffold for the Production of Recombinant Bispecific and Trispecific Antibody Derivatives; J. Immunol. (2000) 165; 7050-7057.
Shen, J. et al., Single Variable Domain Antibody as a Versatile Building Block for the Construction of IgG-like Bispecific Antibodies; Journal of Immunol. Methods 318 (2007) 65-74.
Warren, R.S., et al., Regulation of Vascular Endothelial Growth Factor of Human Colon Cancer Tumorigenesis in a Mouse Model of Experimental Liver Metastasis; J. Clin. Invest., vol. 95 (1995) 1789-1797.
Wu, C., et al., Simultaneous Targeting of Multiple Disease Mediators by a Dual-Variable-Domain Immunoglobulin; Nature Biotechnology, 25:11 (2007) 1290-1297.
Xie, Z., et al., A New Format of Bispecific Antibody: Highly Efficient Heterodimerization, Expression and Tumor Cell Lysis; J. of Immunol. Methods, 296 (2005) 95-101.
European Search Report and Written Opinion dated Aug. 5, 2010.
Morrison et al., Nature Biotech., 15, pp. 159-163 (1997).
Miller, K. et al. (May 1, 2003). "Design, Construction, and In Vitro Analyses of Multivalent Antibodies," J. of Immunology 170(9):4854-4861.
Morrison, S.L. (Nov. 2007). "Two Heads Are Better Than One," Nature Biotechnology 25(11):1233-1234.
Plückthun, A. et al. (1997). "New Protein Engineering Approaches to Multivalent and Bispecific Antibody Fragments," Immunotechnology 3:83-105.
Bendig. "Humanization of Rodent Monoclonal Antibodies by CDR Grafting," Methods: A companion to Methods in Enzymology 8:83-93 (1995).
Myatt et al. "Pathogenic Potential of Human Monoclonal Immunoglobulin Light Chains: Relationship of in vitro Aggregation to in vivo Organ Deposition," Proc. Natl. Acad. Sci. USA 91:3034-3038, (Apr. 1994).
Paul. "Structure and Function of Immunoglobulins," Chapter 9 in Fundamental Immunology, Third Edition, Raven Press, New York, New York, pp. 292-295.
Brooks et al. "A TNF receptor antagonistic scFv, which is not secreted in mammalian cells, is expressed as a soluble mono- and bivalent scFv derivative in insect cells," Immunotechnology 3: 173-184, (1997).
Casset et al. "A peptide mimetic of an anti-CD4 monoclonal" Biochem and Biophys Res Comm. 307:198-205, (2003).
Fiedler and Skerra. "Purification and Characterisation of His-Tagged Antibody Fragments"; in Kontermann and Dubel (Eds.), Antibody Engineering, Springer Lab Manuals, pp. 223-256, (2001).
Leitzgen et al. "Assembly of Immunoglobulin Light Chains as a Prerequisite for Secretion"; Journal of Biological Chemistry 272(5):3117-3123, (1997).
Lodish et al. "Post-Translational Modifications and Quality Control in the Rough ER," Chaper 17, Section 17.6 of Molecular Cell Biology, 4th edition, pp. 707-712, (1999).
Rudikoff et al. "Single amino acid substitution altering antigen-binding specificity," Proc. Natl. Acad. Sci. USA 79: 1979-1983, (1982).
Schlatter et al. "On the Optimal Ratio of Heavy to Light Chain Genes for Efficient Recombinant Antibody Production by CHO Cells," Biotechnol. Prog. 21 :122-133, (2005).
Schmiedl et al. "Effects of Unpaired Cysteines on Yield, Solubility and Activity of Different Recombinant Antibody Constructs Expressed in E. coli" Journal of Immunological Methods 242: 101-114, (2000).
Terpe. "Overview of Tag Protein Fusions: From Molecular and Biochemical Fundamentals to Commercial Systems," Appl Microbiol Biotechnol 60:523-533, (2003).
Van Dijk and Van De Winkel. "Human antibodies as next generation therapeutics," Curr Opin Chem Biol. 5(4): 368-74, (Aug. 2001).
Anonymous. "Production in yeasts of stable antibody fragments," Expert Opinion on Therapeutic Patents 7(2):179-183, (1997).
Bera et al., "A bivalent disulfide-stabilized Fv with improved antigen binding to erbB2," J. Mol. Biol. 281(3):475-483, (Aug. 21, 1998).
Boado et al., "IgG-single chain Fv fusion protein therapeutic for Alzheimer's disease: Expression in CHO cells and pharmacokinetics and brain delivery in the rhesus monkey," Biotechnology and Bioengineering 105(3):627-635, (Feb. 15, 2010).
Brinkmann. "Disulfide-stabilized Fv fragments," Chapter 14 in 2 in Antibody Engineering, Kontermaan et al. eds., vol. 2, Springer-Verlag, Berlin Heidelberg, Germany, pp. 181-189, (Apr. 30, 2010).
Budtschanow et al., "System of Humoral Immunity Antibodies (Theme 2)," Guidance Manual for General Immunology, Twer (2008) p. 3, English Translation, 3 pages.
Caron et al., "Engineered humanized dimeric forms of IgG are more effective antibodies," J. Exp. Med. 176(4):1191-1195, (Oct. 1, 1992).
Carro et al., "Serum insulin-like growth factor I regulates brain amyloid-β levels," Nature Medicine 8(12):1390-1397, (2002, e-pub. Nov. 4, 2002).
Carter., "Bispecific human IgG by design," Immunol. Methods 248:7-15, (2001).

(56) References Cited

OTHER PUBLICATIONS

Davis et al., "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-2002, (2010, e-pub. Feb. 4, 2010).
Deyev., "Multivalency: the hallmark of antibodies used for optimization of tumor targeting by design," Bioessays 30(9):904-918, (2008).
Greenwood et al., "Structural Motifs Involved in Human IgG Antibody Effector Functions,". *Eur. J. Immunology* 23(5):1098-1104, (May 1993).
Grote et al., "Bispecific Antibody Derivatives Based on Full-Length IgG Formats," Chapter 16 in *Methods in Molecular Biology* 901:247-263, (2012).
Hollander., "Bispecific antibodies for cancer therapy," *Immunotherapy* 1(2):211-222, (Mar. 2009).
Hust et al., "Single Chain Fab (scFab) Fragment," *BMC Biotechnology* 7(14):1-15, (Mar. 8, 2007).
Ibragimova et al., "Stability of the β-Sheet of the WW domain: A molecular dynamics simulation study," *Biophysical Journal* 77:2191-2198, (Oct. 1999).
Jakobovits et al., "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6):2551-2555, (Mar. 15, 1993).
Jia et al., "A novel trifunctional IgG-like bispecific antibody to inhibit HIV-1 infection and enhance lysis of HIV by targeting activation of complement," *Virology Journal* 7(142):1-4, (Jun. 29, 2010).
Johnson et al., "Kabat Database and its applications: 30 years after the first variability plot," *Nucleic Acids Research* 28(1):214-218, (2000).
Kabat et al., "Evolutionary and structural influences on light chain constant ($C_L$) region of human and mouse immunoglobulins," *Proc. Natl. Acad. Sci. USA* 72(7):2785-2788, (Jul. 1975).
Kleinschmidt et al., "Design of a modular immunotoxin connected by polyionic adapter peptides," *J. Mol. Biol.* 327(2):445-452, (Mar. 21, 2003).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Krugmann et al., "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Lin et al., "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).
Matrisian. "Cancer biology: extracellular proteinases in malignancy," *Curr. Biol.* 9(20):R776-R778, (Oct. 1999).
Michaelson et al., "Anti-tumor activity of stability-engineered IgG-like bispecific antibodies targeting TRAIL-R2 and LTβR," *MAbs* 1(2):128-141, (Mar. 2009, e-pub. Mar. 11, 2009).
Mimura et al., "Role of Oligosaccharide Residues of IgG1-Fc in FcγRIIb Binding," *The Journal of Biological Chemistry* 276(49): 45539-45547, (Dec. 7, 2001).
Müller et al., "Recombinant Bispecific Antibodies for Cellular Cancer Immunotherapy," *Current Opinion in Molecular Therapeutics* 9:319-326, (2007).
Müller et al., "The first constant domain ($C_H1$ and $C_L$) of an antibody used as heterodimerization domain for bispecific miniantibodies," *FEBS Letters* 422:259-264, (1998).
Orcutt, et al., "A modular IgG-scFv bispecific antibody topology," *Protein Engineering, Design & Selection* 23(4):221-228, (Apr. 2010, e-pub. Dec. 17, 2009).

Pan, Q. et al., "Blocking Neuropilin-1 Function Has an Additive Effect with nti-VEGF to Ihibit Tumor Growth," *Cancer Cell* 11:53-67, (Jan. 2007).
Pleass et al., "Identification of Residues in the CH2/CH3 Domain Interface of IgA Essential for Interaction With the Human Fcα Receptor (Fcα R) CD89," *The Journal of Biology Chemistry* 274(33):23508-23514, (Aug. 13, 1999).
Reiter et al., "Antitumor activity and pharmacokinetics in mice of a recombinant immunotoxin containing a disulfide-stabilized Fv fragment," *Cancer Research* 54:2714-2718, (1994).
Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).
Reiter et al., "Disulfide stabilization of antibody Fv: computer predictions and experimental evaluation," *Protein Engineering* 8:1323-1331, (1995).
Reiter et al., "Construction of a functional disulfide-stabilized TCR Fv indicates that antibody and TCR Fv frameworks are very similar in structure," *Immunity* 2:281-287, (1995).
Reiter et al., "Engineering antibody Fv fragments for cancer detection and therapy: disulfide-stabilized Fv fragments," Nature Biotechnology 14:1239-1245, (1996).
Roitt et al., "Immunology," English Translation by McElroy Translation Company, Moscow "Mir" (2000), p. 110-111, eight pages.
Roitt. et al. "Multispecific Antibodies Comprising Full Length Antibodies and Single Chain Fab Fragments," *Immunology*, English Translation, Moscow:Mir, pp. 388-389, (2000).
Schaefer et al., "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schmiedl et al., "Expression of a bispecific dsFv-dsFv' antibody fragment in *Escherichia coli*," Protein Engineering 13(10):725-734, (Oct. 2000).
Schwartz et al., "A superactive insulin: (B10-aspartic acid]insulin(human)," *Proc. Natl. Acad. Sci. USA* 84:6408-6411, (Sep. 1987).
Shen et al., "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Singer, M. and Berg, P. "Genes and genomes," Moscoer, MIR (Jan. 1998) 63-64 (With English Translation.).
Stevenson et al., "A chimeric antibody with dual Fc regions (bisFabFc) prepared by manipulations at the IgG hinge," *Anticancer Drug Des.* 3(4):219-230, (Mar. 1989).
Stork et al. "A novel tri-functional antibody fusion protein with improved pharmacokinetic properties generated by fusing a bispecific single-chain diabody with an albumin-binding domain from streptococcal protein G," *Protein Eng. Des. Sel.* 20(11):569-576, (Nov. 2007, e-pub. Nov. 3, 2007).
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).
Zeidler et al., "Simultaneous activation of T cells and accessory cells by a new class of intact bispecific antibody results in efficient tumor cell killing," *Journal of Immunology* 163:1246-1252, (1999).
Zuo et al., "An efficient route to the production of an IgG-like bispecific antibody," *Protein Engineering* 13(5):361-367, (2000).
U.S. Appl. No. 14/551,957, filed Nov. 24, 1014 for Castoldi et al.
Aggarwal et al., (Jan. 22, 2008). "Fibroblast Activation Protein Peptide Substrates Identified from Human Collagen I Derived Gelatin Cleavage Sites," *Biochemistry* 47(3):1076-1086.
Ausubel et al., Short Protocols in Molecular Biology, Greene Publishing and Wiley Interscience, New York, New York, (Table of Contents), (1987).
Avgeris et al., "Kallikrein-related peptidase genes as promising biomarkers for prognosis and monitoring of human malignancies," *Biol. Chem* 391(5):505-511, (May 2010).
Bao et al., "HER2-mediated upregulation of MMP-1 is involved in gastric cancer cell invasion," *Arch Biochem Biophys* 499(1-2):49-55, (Jul. 2010).

(56) References Cited

OTHER PUBLICATIONS

Barnes et al., "Advances in animal cell recombinant protein production: GS-NS0 expression system," *Cytotechnology* 32 (2):109-23 (Feb. 2000).

Barnes et al., "Characterization of the stability of recombinant protein production in the GS-NS0 expression system," *Biotechnol Bioeng.* 73(4):261-70 (May 2001).

Baserga et al. (2003). "The IGF-1 receptor in cancer biology," *Int. J. Cancer* 107:873-877.

Bird et al. "Single-Chain Antigen-Binding Proteins," *Science* 242(4877):423-6, (Oct. 21, 1988).

Bird et al. "Single-Chain Antigen-Binding Proteins," *Science* 244(4903):409, *Erratum*, (Apr. 28, 1989).

Boerner et al., "Production of Antigen -Specific Human Monoclonal Antibodies From In Vitro-Primed Human Splenocytes," *J. Immunol.* 147(1):86-95, (Jul. 1991).

Bostrom et al. (2009). "Variants of the antibody herceptin that interact with HER2 and VEGF at the antigen binding site," *Science* 323:1610-1614.

Briggs et al., "Cystatin E/M suppresses legumain activity and invasion of human melanoma," *BMC Cancer* 10(17)1-13, (Jan. 2010).

Brinkmann et al., "A recombinant immunotoxin containing a disulfide-stabilized Fv fragment," *PNAS* 90(16):7538-7542, (1993).

Brorson et al., "Mutational Analysis of Avidity and Fine Specificity of Anti-Levan Antibodies," *J. Immunol.* 163:6694-6701 (1994).

Brüggemann et al., "Comparison of the effector functions of human immunoglobulins using a matched set of chimeric antibodies," *J Exp Med.* 166(5):1351-61, (Nov. 1987).

Brüggemann et al., "Designer Mice: The Production of Human Antibody Repertoires in Transgenic Animals," *Year in Immuno.* 7:33-40, (1993).

Brummell et al., "Probing the combining site of an anti-carbohydrate antibody by saturation-mutagenesis: role of the heavy-chain CDR3 residues," *Biochemistry* 32(4):1180-1187 (1993).

Brunhouse et al., "Isotypes of IgG: comparison of the primary structures of three pairs of isotypes which differ in their ability to activate complement," *Mol Immunol.* 16(11): 907-917 (Nov. 1979).

Burgess et al. "Possible dissociation of the heparin-binding and mitogenic activities of heparin-binding (acidic fibroblast growth factor-1 from its receptor-binding activities by site-directed mutagenesis of a single lysine residue," *Journal of Cell Biology* 111:2129-2138, (Nov. 1990).

Burks et al., "In vitro scanning saturation mutagenesis of an antibody binding pocket," *PNAS* 94(2):412-417 (1997).

Burton et al., "The C1q Receptor Site on Immunoglobulin G," *Nature* 288(5789):338-344, (Nov. 27, 1980).

Carter et al., "Humanization of an Anti-P185$^{HER2}$ Antibody for Human Cancer Therapy," *Proc Natl Acad Sci USA.* 89(10): 4285-4289 (May 1992).

Castoldi et al. (2012). "Molecular characterization of novel trispecific ErbB-cMet-IGF1R antibodies and their antigen-binding properties," *Prot. Engin. Des. Selection* 25:551-560.

Chernaia. (Sep.-Oct. 1998). "[Cathepsin L from human brain tumor. Purification and contents]." Ukr Biokhim Zh. 70(5):97-103 (English Translation of Abstract.) (Article in Russian).

Chitnis et al., "The type 1 insulin-like growth factor receptor pathway," *Clin. Cancer Res.* 14(20):6364-6370, (Oct. 16, 2008).

Chung et al., "Development of a novel albumin-binding prodrug that is cleaved by urokinasetype-plasminogen activator (uPA)," *Bioorg Med Chem Lett.* 16(19):5157-5163 (Oct. 1, 2006).

Cohen et al., "Nonchromosomal antibiotic resistance in bacteria: Genetic transformation of *Escherichia coli* by R-factor DNA," *Proc. Natl. Acad. Sci. USA* 69(8):2110-2114 (Aug. 1972).

Cole et al., "The EBV-hybridoma technique and its application to human lung cancer," *Monoclonal Antibodies and Cancer Therapy*, New York: Alan R. Liss, Inc. pp. 77-96 1985.

Coleman., "Effects of amino acid sequence changes on antibody-antigen interactions," *Research in Immunol.* 145(1):33-38, (1994).

Cordingley et al., "Substrate requirements of human rhinovirus 3C protease for peptide cleavage in vitro," *J. Biol. Chem.* 265(16):9062-9065, (1990).

Cortesio et al. (Mar. 10, 2008). "Calpain 2 and PTP1B function in a novel pathway with Src to regulate invadopodia dynamics and breast cancer cell invasion," *J. Cell Biol.* 180(5):957-971.

Crawford et al., "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).

Cudic et al., "Extracellular proteases as targets for drug development," *Curr. Protein Pept Sci* 10(4):297-307, (Aug. 2009).

Cuesta et al. (2010). "Multivalent antibodies: when design surpasses evolution," *Trends Biotech.* 28:355-362.

Cullen et al., "Granzymes in cancer and immunity," *Cell Death Differ* 17(4):616-623, (Apr. 2010).

Dall'Acqua, W. et al. (1998). "Contribution of Domain Interface Residues to the Stability of Antibody CH3 Domain Homodimers", *Biochemistry*, 37:9266-9273.

Davies et al., "Expression of GnTIII in a recombinant anti-CD20 CHO production cell line: Expression of antibodies with altered glycoforms leads to an increase in ADCC through higher affinity for FcγRIII," *Biotechnol. Bioeng.* 74:288-294, (2001).

Dimmock, N.J. et al. (2004). "Valency of antibody binding to virions and its determination by surface plasmon resonance", *Rev. Med. Virol.*, 14:123-135.

Donaldson et al., "Design and development of masked therapeutic antibodies to limit off-target effects: Application to anti-EGFR antibodies," *Cancer Biology & Therapy* 8(22):2145-2150, (Nov. 15, 2009).

Durocher et al., "High-level and high-throughput recombinant protein production by transient transfection of suspension-growing human 293-EBNA1 cells," *Nucleic Acids Research* 30(2 e9):nine pages, (2002).

Dufner et al., "Harnessing phage and ribosome display for antibody optimization," *Trends Biotechol.* 24(11):523-29 (2006).

Edelman et al., "The covalent structure of an entire γG immunoglobulin molecule," *Proc. Natl. Acad. Sci. USA* 63:78-85, (1969).

Fenn, S. et al., "Crystal Structure of an Anti-Ang2 CrossFab Demonstrates Complete Structural and Functional Integrity of the Variable Domain" PLoS One 8(4):e61953 (Apr. 1, 2013).

Flatman et al., "Process analytics for purification of monoclonal antibodies," *J. Chromatogr B* 848:79-87, (2007).

Galamb et al., "Inflammation, adenoma and cancer: objective classification of colon biopsy specimens with gene expression signature," *Dis Markers* 25(1):1-16, (2008).

Geisse et al., "Eukaryotic expression systems: A comparison," *Protein Expression and Purification* 8:271-282 (1996).

Gerspach et al., "Target-selective activation of a TNF prodrug by urokinase-type plasminogen activator (uPA) mediated proteolytic processing at the cell surface," *Cancer Immunol. Immunother* 55:1590-1600 (2006).

Gold et al., "A novel bispecific, trivalent antibody construct for targeting pancreatic carcinoma," *Cancer Res.* 68(12):4819-4826, (2008).

Goldenberg et al., "Bi-Specific Antibodies that Bind Specific Target Tissue and Targeted Conjugates," Derwent Information Ltd., 12 pages, (2012).

Graham et al., "A new technique for the assay of infectivity of human adenovirus 5 DNA," *Virology* 52 (2):456-467, (1973).

Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).

Hartog et al., "The Insulin-like growth factor 1 receptor in cancer: Old focus, new future," European Journal of Cancer, Pergamon Press, Oxford, GB, 43(13):1895-1904, (Aug. 23, 2007).

Henry et al., "Clinical implications of fibroblast activation protein in patients with colon cancer," *Clin Cancer Res.* 13(6):1736-1741, (Mar. 15, 2007).

(56) References Cited

OTHER PUBLICATIONS

Hezareh et al., "Effector Function Activities of a Panel of Mutants of a Broadly Neutralizing Antibody against Human Immunodeficiency Virus Type 1," *Journal of Virology* 75(24):12161-12168, (Dec. 2001).
Hoogenboom and Winter., "By-passing immunisation. Human antibodies from synthetic repertoires of germline $V_H$ gene segments rearranged in vitro," *J Mol Biol.* 227 (2):381-388, (Sep. 20, 1992).
Huston, J.S. et al. (1993). "Medical Applications of Single-Chain Antibodies," *Intern. Rev. Immunol.* 10(2-3):195-217.
Huston et al. "Protein engineering of antibody binding sites: recovery of specific activity in an anti-digoxin single-chain Fv analogue produced in *Escherichia coli*," *Proc. Natl. Acad. Sci. U.S.A.* 85(16):5879-5883, (Aug. 1988).
Idusogie et al., "Mapping of the C1q binding site on rituxan, a Chimeric antibody with a human IgG1Fc," *The Journal of Immunology* 164:4178-4184, (2000).
Jakobovits et al., "Germ-line Transmission and Expression of a Human-derived Yeast Artificial Chromosome," *Nature* 362:255-258, (Mar. 1993).
Jang et al., "The structural basis for DNA binding by an anti-DNA autoantibody," *Mol. Immunol.* 35(18):1207-1217 (1998).
Jefferis et al., "IgG-Fc-mediated effector functions: molecular definition of interaction sites for effector ligands and the role of glycosylation," *Immunol Rev.* 163:59-76, (1998).
Johnson et al. "Construction of single-chain Fv derivatives monoclonal antibodies and their production in *Escherichia coli*," *Methods Enzymol.* 203:88-98, (1991).
Kabat et al., Sequences of Proteins of Immunological Interest (Table of Contents and Introduction), 5th edition, Bethesda, MD: Public Health Service, NIH, vol. 1, (1991).
Karadag et al., "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 2006).
Kaufman., "Overview of Vector Design for Mammalian Gene Expression," *Molecular Biotechnology* 16:151-160, (2000).
Kazama et al., "Hepsin, a putative membrane-associated serine protease, activates human factor VII and initiates a pathway of blood coagulation on the cell surface leading to thrombin formation," *JBC* 270:66-72, (1995).
Klein, C. et al., "Progress in overcoming the chain association issue in bispecific heterodimeric IgG antibodies" mAbs 4(6):653-663 ( 2012).
Kobayashi et al., "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi et al. "Tryptophan H33 plays an important role in pyrimidine (6-4) pyrimidone photoproduct binding by a high-affinity antibody," *Protein Engineering* 12(10):879-844 (1999).
Lamkanfi et al., "Inflammasomes: guardians of cytosolic sanctity," *Immunol. Rev.* 227(1):95-105, (Jan. 2009).
Lazar et al., "Transforming growth factor α: Mutation of aspartic acid 47 and leucine 48 results in different biological activities," Molecular and Cellular Biology 8(3):1247-1252, (Mar. 1988).
Lee et al., "Using substrate specificity of antiplasmin-cleaving enzyme for fibroblast activation protein inhibitor design," *Biochemistry* 48(23):5149-5158, (Jun. 16, 2009).
Leeman et al., "The Structure, Regulation, and Function of Human Matrix Metalloproteinase-13," *Crit. Rev Biochem Mol. Biol.* 37(3):149-166, (2002).
Lifely et al., "Glycosylation and Biological Activity of CAMPATH-1H Expressed in Different Cell Lines and Grown Under Different Culture Conditions," *Glycobiology* 5(8):813-822, (Dec. 1995).
Liotta et al., "Metastatic potential correlates with enzymatic degradation of basement membrane collagen," *Nature* 284(5751) 67-68, (Mar. 6, 1980).

Liu et al., "Clinical and imaging diagnosis of primary hepatic lymphoma," *J First Mil Med. Univ,* 25(10):1290-1292, three pages, (2005). (Translation of the Abstract Only.).
Lopez-Otin et al., "The regulatory crosstalk between kinases and proteases in cancer," *Nat. Rev. Cancer* 10(4):278-292, (Apr. 2010).
Love et al., "Recombinant antibodies possessing novel effector functions," *Methods in Enzymology* 178:515-527, (1989).
Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al., "ADAMTS1 and MMP1 proteolytically engage EGF-like ligands in an osteolytic signaling cascade for bone metastasis," *Genes Dev.* 23(16):1882-1894, (Aug. 2009).
Lukas et al., "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al., "Oligosaccharide-protein interactions in IgG can modulate recognition by Fcγ receptors," *FASEB Journal* 9:115-119, (1995).
Makrides., "Components of Vectors for Gene Transfer and Expression in Mammalian Cells," *Protein Expression and Purification* 17:183-202, (1999).
Mamoune et al., "Calpain-2 as a target for limiting prostate cancer invasion," *Cancer Res.* 63(15):4632-4640, (Aug. 2003).
Marks et al., "By-Passing Immunization: Human Antibodies From V-gene Libraries Displayed on Phage," *J Mol Biol.* 222(3) :581-597, (Dec. 5, 1991).
Marvin et al., "Bispecific antibodies for dual-modality cancer therapy: killing two signaling cascades with one stone," *Curr. Opin. Drug Discov. Devl.* 9:184-193, (2006).
Marvin et al., "Recombinant approaches to IgG-like bispecific antibodies," *Acta Pharmacol. Sin.* 26:649-658, (2005).
McLean, G.R. et al. (2005). "A point mutation in the CH3 domain of human IgG3 inhibits antibody secretion without affecting antigen specificity", *Molecular Immunology*, 42:1111-1119.
Meissner et al., "Transient Gene Expression: Recombinant Protein Production with Suspension-Adapted HEK293-EBNA Cells," *Biotechnology and Bioengineering* 75:197-203, (2001).
Metz et al. (2012). "Bispecific antibody derivatives with restricted binding functionalities that are activated by proteolytic processing," *Prot. Engin. Des. Selection* 25:571-580.
Milstein et al., "Hybrid Hybridomas and Their Use in Immunohistochemistry," *Nature* 305: 537-540, (Oct. 6, 1983).
Minn et al., "Genes that Mediate Breast Cancer Metastasis to Lung," *Nature* 436(7050):518-524, (Jul. 2005).
Mirny, L. et al. (2001). "Protein Folding Theory: From Lattice to All-Atom Models", *Annu. Rev. Biophys. Biomol. Struct.*, 30:361-96.
Morgan et al., "The N-terminal End of the $C_H2$ Domain of Chimeric Human IgG1 anti-HLA-DR is Necessary for C1q, FcγRI and FcγRIII Binding," *Immunology* 86:319-324, (1995).
Morrison. "Success in Specification," *Nature* 368:812-813, (Apr. 1994).
Morrison et al., "Variable region domain exchange influences the functional properties of IgG," *Journal of Immunology, American Association of Immunologists* 160:2802-2808, (Jan. 1, 1998).
Müller et al., "Bispecific Antibodies," Chapter 2 in Handbook of Therapeutic Antibodies, Dübel, S. ed., Wiley-VCH Verlag GmbH & Company KGaA, Weinheim, pp. 345-378, (2007).
Mukhopadhyay et al., "Matrix metalloproteinase-12 is a therapeutic target for asthma in children and young adults," *J. Allergy Clin Immunol.* 126:70-76, (2010).
Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and Pump (matrilysin)," *Biochemistry* 32(25):6427-6432, (Jun. 29, 1993).
Neuberger et al., "A hapten-specific chimaeric IgE antibody with human physiological effector function," *Nature* 314:268-270, (Mar. 21, 1985).

(56) References Cited

OTHER PUBLICATIONS

Niwa et al., "IgG subclass-independent improvement of antibody-dependent cellular cytotoxicity by fucose removal from $Asn^{297}$-linked oligosaccharides," *J. Immunol. Methods* 306:151-160, (2005).
Norderhaug et al., "Versatile Vectors for Transient and Stable Expression of Recombinant Antibody Molecules in Mammalian Cells," *Journal of Immunological Methods* 204:77-87, (1997).
Novotný, J. et al. (1985). "Structural invariants of antigen binding: Comparison of immunoglobulin $V_L$-$V_H$ and $V_L$- $V_L$ domain dimmers", *Proc. Natl. Acad. Sci. USA*, 82:4592-4596.
Ohno et al., "Antigen-binding specificities of antibodies are primarily determined by seven residues of $V_H$," *Proc. Natl. Acad. Sci. USA* 82(9):2945-2949, (May 1985).
Orlandi et al., "Cloning Immunoglobulin Variable Domains for Expression by the Polymerase Chain Reaction," *Proc. Natl. Acad. Sci. USA* 86:3833-3837, (May 1989).
Pace et al., "How to Measure and Predict the Molar Absorption Coefficient of a Protein," *Protein Science* 4(11): 2411-2423, (Nov. 1995).
Pakula et al., "Genetic analysis of protein stability and function," *Annu. Rev. Genet.* 23:289-310, (1989).
PreScission Protease, GE Healthcare Catalogue No. 27/0843-01, located at http://www.gelifesciences.com/webapp/wcs/stores/servlet/productById/en/GELifeScience, last visited on Jul. 10, 2013, one page.
Radaev et al., "Recognition of IgG by Fcγ Receptor," *The Journal of Biological Chemistry* 276(19): 16478-16483, (May 11, 2001).
Rajagopal et al., "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).
Rawlings., "A large and accurate collection of peptidase cleavages in the MEROPS database," Database (Oxford), pp. 1-14, (2009, e-pub. Nov. 2, 2009).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al. "Improved binding and antitumor activity of a recombinant anti-erbB2 immunotoxin by disulfide stabilization of the Fv fragment," *JBC* 269:18327-18331, (1994).
Reiter et al. "Engineering interchain disulfide bonds into conserved framework regions of Fv fragments: improved biochemical characteristics of recombinant immunotoxins containing disulfide-stabilized Fv," *Protein Eng.* 7(5):697-704, (May 1994).
Reiter et al., "Cytotoxic and antitumor activity of a recombinant immunotoxin composed of disulfide-stabilized anti-Tac Fv fragment and truncated *Pseudomonas* exotoxin," *International Journal of Cancer* 58:142-149, (1994).
Riechmann et al., "Reshaping Human Antibodies for Therapy," *Nature* 332:323-327, (Mar. 24, 1988).
Routier et al., "The Glycosylation Pattern of a Humanized IgGI Antibody (D1.3) Expressed in CHO Cells," *Glycoconjugate Journal* 14:201-207, (1997).
Ruppert et al., "Protease levels in breast, ovary and other gynecological tumor tissues: prognostic importance in breast cancer," *Cancer Detect. Prev.* 21(5):452-459, (1997).
Sambrook et al., Molecular Cloning: A Laboratory Manual "The Table of Contents" Cold Spring Harbor, New York: Cold Spring Harbor Laboratory Press, (1989).
Schlaeger., "The Protein Hydrolysate, Primatone RL, is a Cost Effective Multiple Growth Promoter of Mammalian Cell Culture in Serum-containing and Serum-free Media and Displays Anti-apoptosis Properties," *Journal of Immunological Methods* 194:191-199, (1996).
Schlaeger et al., "Transient Gene Expression in Mammalian Cells Grown in Serum-free Suspension Culture," *Cytotechnology* 30:71-83, (1999).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Scott et al., "Biologic protease inhibitors as novel therapeutic agents," *Biochimie* 92(11):1681-1688, (Nov. 2010).
Shields et al., "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al., "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al., "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Simmons et al., "Expression of full-length immunoglobulins in *Escherichia coli*: Rapid and Efficient production of aglycosylated antibodies," *Journal of Immunological Methods* 263:133-147, (2002).
Simon et al., "Antibody Domain Mutants Demonstrate Autonomy of the Antigen Binding Site," *The EMBO Journal* 9(4):1051-1056, (1990).
Stetler-Stevenson et al., "Progelatinase a activation during tumor cell invasion," *Invasion Metastasis* 14(1-6):259-268, (1994-1995).
Thommesen et al., "Lysine 322 in the human IgG3 $C_H2$ domain is crucial for antibody dependent complement activation," *Molecular Immunology* 37:995-1004, (2000).
Torres, M. et al. (2005). "Variable-Region-Identical Antibodies Differing in Isotype Demonstrate Differences in Fine Specificity and Idiotype", *The Journal of Immunology*, 174:2132.
Tripathi et al., "Laminin-332 is a substrate for hepsin, a protease associated with prostate cancer progression," *JBC* 283:30576-30584, (2008).
Ueki et al. (1997). "Expression of hepatocyte growth factor and its receptor c-met proto-oncogene in hepatocellular carcinoma," *Hepatology* 25(4):862-866.
Umaña et al., "Engineered Glycoforms of an Antineuroblastoma IgG1 with Optimized Antibody-Dependent Cellular Cytotoxic Activity," *Nature Biotechnology* 17(2):176-180 (Feb. 1999).
Van Dijk and Van De Winkel., "Human antibodies as next generation therapeutics," *Curr Opin Chem Biol.* 5(4): 368-74, (Aug. 2001).
Van Spriel et al., "Immunotherapeutic perspective for bispecific antibodies," *Immunology Today* 21(8):391-397, (Aug. 2000).
Van'T Veer et al., "Gene expression profiling predicts clinical outcome of breast cancer," *Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Veveris-Lowe et al., "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi., "Antibody Purification Methods," *Applied Biochemistry and Biotechnology* 75:93-102, (1998).
Walker et al., "Efficient and Rapid Affinity Purification of Proteins Using Recombinant Fusion Proteases," *Bio/Technology* 12:601-605, (1994).
Wallash et al. (1995). "Heregulin-dependent regulation of HER2/neu oncogenic signaling by heterodimerization with HER3," *EMBO J.* 14:4267-4275.

(56) References Cited

OTHER PUBLICATIONS

Webber et al., "Preparation and characterization of a disulfide-stabilized Fv fragment of the anti-Tac antibody: comparison with its single-chain analog," *Molecular Immunology* 32:249-258, (1995).
Werner et al., "Appropriate Mammalian Expression Systems for Biopharmaceuticals," *Drug Research* 48(8):870-880, (1998).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Willems et al., "Optimizing expression and purification from cell culture medium of trispecific recombinant antibody derivatives," *Journal of Chromatography B* 786:161-176, (2003).
Woof et al., "Human antibody-Fc receptor interactions illuminated by crystal structures," *Nat. Rev. Immunol.* 4:1-11, (2004).
Wright et al., "ADAM28: a potential oncogene involved in asbestos-related lung adenocarcinomas," *Genes Chromosomes Cancer* 49(8);688-698, (Aug. 2010).
Wright and Morrison, "Effect of Glycosylation on Antibody Function: Implications for Genetic Engineering," *Trends in Biotechnology* 15:26-32, (1997).
Anthony et al. "A recombinant IgG Fc that recapitulates the antiinflammatory activity of IVIG," *Science* 320(5874):373-376, (2008).
Armour et al. "Recombinant human IgG molecules lacking Fcγ receptor I binding and monocyte triggering activities," *Eur. J. Immunol.* 29:2613-2624, (1999).
Beckman et al. "Antibody Constructs in Cancer Therapy. Protein Engineering Strategies to Imporve Exposure in Solid Tumors," *Cancer* 109(2):170-179, (Jan. 15, 2007, e-pub. Dec. 11, 2006).
Carter. "Potent antibody therapeutics by design," *Nature Reviews Immunology* 6:343-357, (2006).
Céspedes et al. "Mouse Models in Oncogeneis and Cancer Therapy," *Clin. Tranl. Oncol.* 8(5):318-329 (2006).
Chames et al. "Bispecific antibodies for cancer therapy", *Current Opinion in Drug Discovery & Development*, 12(2):276-283, (2009).
Chan et al. "Therapeutic antibodies for autoimmunity and inflammation," *Nat. Rev. Immunol.* 10(5):301-316, (2010).
Charlton. In: Methods in Molecular Biology, vol. 248, Lo, B.K.C. (ed.), Humana Press, Totowa, NJ, pp. 245-254, (2003).
Chicheportiche et al."TWEAK, a New Secreted Ligand in the Tumor Necrosis Factor Family That Weakly Induces Apoptosis,"*J. Biol. Chem.* 272(51):32401-32410, (1997).
Chin et al. "Addition of p-azido-L-phenylalanine to the genetic code of *Escherichia coli,*"*J. Am. Chem. Soc.* 124(31):9026-9027, (2002).
Chin et al. "In vivo photocrosslinking with unnatural amino Acid mutagenesis," *ChemBioChem.* 3(11):1135-1137, (2002).
Chin et al. "Addition of a photocrosslinking amino acid to the genetic code of *Escherichia coli,"* Proc. Natl. Acad. Sci. U.S.A. 99(17):11020-11024, (2002).
Clancy et al. "Sortase transpeptidases: insights into mechanism, substrate specificity, and inhibition," *Biopolymers* 94(4):385-396, (2010).
Cruse, et al., 2nd ed., CRC Press, pp. 37, 316-317, (2003).
Dennis."Off by A Whisker," *Nature* 442:739-741, (2006).
Friend et al. "Phase I study of an engineered aglycosylated humanized CD3 antibody in renal transplant rejection," *Transplantation*, 68(11):1632-1637, (1999).
Fujimori et al. "A Modeling Analysis of Monoclonal Antibody Percolation Through Tumors: A Binding-Site Barrier," *J. Nuc. Med.* 31(7):1191-1198, (Jul. 1990).
Gerngross. "Advances in the production of human therapeutic proteins in yeasts and filamentous fungi," *Nat. Biotech.* 22:1409-1414, (2004).
Hatfield et al. "Antiangiogenic therapy in acute myelogenous leukemia: targeting of vascular endothelial growth factor and interleukin 8 as possible antileukemic strategies," *Curr. Cancer Drug Targets*, 5(4):229-248, (2005).
Hellings et al., "Interleukin-17 orchestrates the granulocyte influx into airways after allergen inhalation in a mouse model of allergic asthma" *AM J RESPIR CELL MOL BIOL* 28:42-50 (2003).

Herberman. "Immunodiagnosis of Cancer", in Fleisher (ed.), "The Clinical Biochemistry of Cancer," *American Association of Clinical Chemists*, p. 347, (1979).
Huber et al. "Crystallographic structure studies of an IgG molecule and an Fc fragment," *Nature* 264:415-420, (1976).
Hudson et al. "Engineered antibodies," Nat. Med. 9:129-134, (2003).
Ilangovan et al. "Structure of sortase, the transpeptidase that anchors proteins to the cell wall of Staphylococcus aureus," *Proc. Natl. Acad. Sci. U.S.A.* 98(11):6056-6061, (2001).
Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Jefferis et al. "Interaction sites on human IgG-Fc for FcγR: current models," *Immunol. Lett.* 82:57-65, (2002).
Jiang et al. "Advances in the assessment and control of the effector functions of therapeutic antibodies," *Nat. Rev. Drug Discov.* 10(2):101-111, (2011).
Komiyama et al. "IL-17 plays an important role in the development of experimental autoimmune encephalomyelitis" *J Immunol* 177:566-573, ( 2006).
Kotake et al. "IL-17 in synovial fluids from patients with rheumatoid arthritis is a potent stimulator of osteoclastogenesis,"J. Clin. Invest. 103:1345-1352, (1999).
Kumar et al. ":Molecular Cloning and Expression of the Fabs of Human Autoantibodies in *Escherichia coli,"* J. Biol. Chem. 275(45):35129-35136, (Nov. 10, 2000).
Labrijn et al. "Species-Specific Determinants in the IgG CH3 Domain Enable Fab-Arm Exhange by Affecting the Noncovalent CH3-CH3 Interaction Strength," *The Journal of Immmunology* 187:3238-3246, (2011, e-pub. Aug. 12, 2011).
Levary et al. "Protein-Protein fusion catalyzed by sortase A," PLOS One 6:e18342.1-e18342.6, (2011).
Li et al. "Optimization of humanized IgGs in glycoengineered *Pichia pastoris,*" Nat. Biotech. 24:210-215, (2006).
Lynch et al. "TWEAK Induces Angiogenesis and Proliferation of Endothelial Cells," *J. Biol. Chem.* 274:8455-8459, (1999).
Madej et al. "Engineering of an anti-epidermal growth factor receptor antibody to single chain format and labeling by sortase A-mediated protein ligation," *Biotechnology and Bioengineering* 109(6):1461-1470, (2012).
Mallender et al "Comparative Properties of the Single Chain Antibody and Fv Derivateives of mAb 4-4-20. Relationship Between Interdomain Interactions and the High Affinity for Fluorescein Ligand," *Journal of Biological Chemistry* 271(10):5338-5346, (Mar. 8, 1996).
Marsters et al. "Identification of a Ligand for the Death-Domain-Containing Receptor Apo3," *Curr. Biol.* 8:525-528, (1998).
Matusevicius et al. "Interleukin-17 mRNA Expression in Blood and CSF Mononuclear Cells is Augmented in Multiple Sclerosis," *Multiple Sclerosis* 5:101-104, (1999).
Mizukami et al. "Induction of interleukin-8 preserves the angiogenic response in HIF-1alpha-deficient colon cancer cells," *Nat. Med.* 11(9):992-997, (2005).
Möhlmann et al. "In vitro sortagging of an antibody fab fragment: overcoming unproductive reactions of sortase with water and lysine side chains," *Chembiochem: A European Journal of Chemical Biology*, 12(11):1774-1780, (2011).
Noren et al. "A General Method for Site-Specific Incorporation of Unnatural Amino Acids into Protein,s" *Science* 244:182-188, (1989).
Novellino et al. "A listing of human tumor antigens recognized by T cells: Mar. 2004 update," *Cancer Immunol. Immunother*, 54(3):187-207, (2005).
Parmiani et al. "Unique human tumor antigens: immunobiology and use in clinical trials," *J. Immunol.* 178(4):1975-1979, (2007).
Paul. Fundamental Immunolgy, Chapter "Immunoglobulins: Structure and Function," Jeske, D.D. et al., New York, New York, Raven Press, p. 131-165, (1984). (1 page translation of 7.9.1 Disculfide Bonds).
Popp et al. "Making and breaking peptide bonds: protein engineering using sortase," *Angewandte Chemie* 50(22):5024-5032, (2011).

(56) References Cited

OTHER PUBLICATIONS

Presta. "Molecular engineering and design of therapeutic antibodies," *Current Opinion in Immunology* 20:460-470, (2008).
Ren et al. "Macrophage migration inhibitory factor stimulates angiogenic factor expression and correlates with differentiation and lymph node status in patients with esophageal squamous cell carcinoma," *Ann. Surg.* 242:55-63, (2005).
Routledge et al. "The effect of aglycosylation on the immunogenicity of a humanized therapeutic CD3 monoclonal antibody," *Transplantation*, 60(8):847-853, (1995).
Roux et al. "Comparisons of the ability of human IgG3 hinge mutants, IgM, IgE, and IgA2, to form small immune complexes: a role for flexibility and geometry," *J. Immunol.* 161(8):40834090, (1998).
Rudnick et al. "Affinity and Avidity in Antibody-Based Tumor Targeting," *Cancer Biotherapy & Radiopharmaceuticals* 24(2):155-162 (2009).
Sakamoto et al. "Enzyme-Mediated Site-Specific Antibody-Protein Modification Using a ZZ Domain as a Linker,"*BioConjugate Chem..* 21 :2227-2293 (2010, e-pub. Nov. 11, 2010).
Salfeld. "Isotype Selection in Antibody Engineering," *Nat. Biotechnol.* 25(12):1369-1372, (Dec. 2007).
Sensi et al. "Unique tumor antigens: evidence for immune control of genome integrity and immunogenic targets for T cell-mediated patient-specific immunotherapy," *Clin. Cancer Res.* 12(17):5023-5032, (2006).
Smith-Gill et al. "Contributions of Immunoglpbulin Heavy and Light Chains 5o Antibody Specificity for Lysozyme and Two Haptens," *J. Immunol.* 139(12):4135-4144, (Dec. 15, 1987).
Sondermann et al. "The 3.2-A crystal structure of the human IgG1 Fc fragment-FcyRIII complex," *Nature* 406:267-273, (2000).
Song et al."Light Chain of Natural Antibody Plays a Dominant Role in Protein Antigen Binding," *Biochem. Biophys. Res. Comm.* 268(2):390-394, (Feb. 16, 2000).
Strop et al. "Generating Bispecific Human IgG1 and IgG2 Antibodies from Any Antibody Pair," *Journal of Molecular Biology* 420(3):204-219, (2012).
Ta et al. "Enzymatic Single-Chain Antibody Tagging a Universal Approach to Targeted Molecular Imaging and Cell Homing in Cardiovascular Disease," *Circulation Research*, 109(4):365-373, (2011).
Talmadge et al. "Murine Models to Evaluate Novel and Conventional Therapeutic Strategies for Cancer," *Am. J. Pathol.* 170(3):793-804, (Mar. 2007).
Thies et al. (1999). "Folding and association of the antibody domain CH3: prolyl isomerization preceeds dimerization," *J. Mol. Biol.*, 293:67-79, (1999).
Thurber et al. "Antibody Tumor Penetration: Transport Opposed by Systemic and Antigen-Mediated Clearance," *Adv. Drug Deliv. Rev.* 60(12):1421-1434, (Sep. 2008, E-Pub. Apr. 24, 2008).
Ton-That et al. "Purification and characterization of sortase, the transpeptidase that cleaves surface proteins of Staphylococcus aureus at the LPXTG motif," *Proc. Natl. Acad. Sci. U.S.A.* 96(22):12424-12429, (1999).
Tsukiji et al. "Sortase-Mediated Ligation: A Gift from Gram-Positive Bacteria to Protein Engineering," *Chembiochem*, 10(5):787-798, (2009).
Vallböhmer et al. "Molecular determinants of cetuximab efficacy," *J. Clin. Oncol.* 23(15):3536-3544, (May 20, 2005).
Voskoglou-Nomikos et al. "Clinical Predictive Value of the *in Vitro* Cell Line, Human Xenograft, and Mouse Allograft Preclinical Cancer Models," *Clin. Can. Res.* 9:4227-4239, (Sep. 15, 2003).
Wagner et al. "Bispecific antibody generated with sortase and click chemistry has broad antiinfluenza virus activity," *Proc. Natl. Acad. Sci. USA* 111:16820-16825, (Nov. 25, 2014).
Wang et al. "Expanding the genetic code", *Chem. Commun (Camb.)*, 7:1-11, (2002).
Ward et al. "The effector functions of immunoglobulins: implications for therapy," *Ther. Immunol.* 2:77-94, (1995).
Ward et al. "Binding Activities of a Repertoire of Single Immunoglobulin Variable Domains Secreted From *Escherichia coli*,"*Nature* 341:544-546, (Oct. 12, 1989).
Witte et al. "Preparation of unnatural N-to-N. And C-to-C protein fusions", *Proceedings of the National Academy of Sciences of the United States of America*, 109(30):11993-11998, (2012).
Yazaki et al. Methods in Molecular Biology, vol. 248, Lo, B.K.C. (ed.), Humana Press, Totowa, NJ, pp. 255-268, (2004).
Ziolkowska et al. "High Levels of IL-17 in Rheumatoid Arthritis Patients: IL-15 Triggers in Vitro IL-17 Production Via Cyclosporin A-Sensitive Mechanism," *J. Immunol.* 164:2832-2838, (2000).
International Search Report mailed on Sep. 9, 2015, for PCT Application No. PCT/EP2015/057165, filed on Apr. 1, 2015, 5 pages.
Written Opinion mailed on Sep. 9, 2015, for PCT Application No. PCT/EP2015/057165, filed on Apr. 1, 2015, 7 pages.
International Search Report mailed on Aug. 5, 2014, for PCT Patent Application No. PCT/EP2013/063258, filed on Jun. 25, 2013, seven pages.
Written Opinion of the International Searching Authority mailed on Aug. 5, 2014, for PCT Patent Application No. PCT/EP2013/063258, filed on Jun. 25, 2013, seven pages.
International Search Report mailed on Jul. 29, 2013, for PCT Patent Application No. PCT/EP2013/060529, filed on May 22, 2013, seven pages.
International Search Report mailed on Dec. 6, 2011, for PCT Patent Application No. PCT/EP2011/064476 filed on Aug. 23, 2011, seven pages.
International Search Report mailed on Dec. 6, 2011, for PCT Patent Application No. PCT/EP2011/064468 filed on Aug. 23, 2011, seven pages.
Written Opinion of the International Searching Authority mailed on Jul. 29, 2013, for PCT Patent Application No. PCT/EP2013/060529, filed on May 22, 2013, seven pages.
Written Opinion of the International Searching Authority mailed on Dec. 6, 2011, for PCT Patent Application No. PCT/EP2011/064476 filed on Aug. 23, 2011, four pages.
Written Opinion of the International Searching Authority mailed on Dec. 6, 2011, for PCT Patent Application No. PCT/EP2011/064468 filed on Aug. 23, 2011, four pages.
European Search Report dated Mar. 14, 2006, for European Patent Application No. 07024864.6, 8 pages.
European Search Report dated Aug. 31, 2009, for European Patent Application No. 09005108.7, 6 pages.
U.S. Appl. No. 14/579,165, filed on Dec. 22, 2014, by Dieter et al.
U.S. Appl. No. 14/579,192, filed on Dec. 22, 2014, by Sebastian et al.
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
Chen et al. "Improved Variants of SrtA for Site-Specific Conjugation on Antibodies and Proteins With High Efficiency," *Scientific Reports* 6(31899):1-12, (Aug. 18, 2016).
Nagaoka et al. "Single Amino Acid Substitution in the Mouse IgG1 Fc Region Induces Drastic Enhancement of the Affinity to Protein A," *Protein Engineering* 16(4):243-245, (2003).
Rose et al. "Quantitative Analysis of the Interaction Strength and Dynamics of Human IgG4 Half Molecules by Native Mass Spectrometry," *Structure* 19:1274-1282, (Sep. 7, 2011).
U.S. Appl. No. 15/279,738.
U.S. Appl. No. 15/279,799.
U.S. Appl. No. 15/281,484.
U.S. Appl. No. 15/281,493.
U.S. Appl. No. 15/280,372.
U.S. Appl. No. 15/282,994.
PCT Application No. PCT/EP2016/073167.
PCT Application No. PCT/EP2016/073175.
PCT Application No. PCT/EP2016/073176.

\* cited by examiner

SEQUENCE LISTING

```
<160> NUMBER OF SEQ ID NOS: 11

<210> SEQ ID NO 1
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Unmodified heavy chain <Ang-2> with C-terminal
      fused <VEGF> VH-CL domains of modified Fab Fragment (CH1-CL
      exchange)

<400> SEQUENCE: 1

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80
Met Glu Leu Ser Arg Leu Arg Ser Asp Thr Ala Val Tyr Tyr Cys
             85                  90                  95
Ala Arg Ser Pro Asn Pro Tyr Tyr Asp Ser Ser Gly Tyr Tyr Tyr
            100                 105                 110
Pro Gly Ala Phe Asp Ile Trp Gly Gln Gly Thr Met Val Thr Val Ser
            115                 120                 125
Ser Ala Ser Thr Lys Gly Pro Ser Val Phe Pro Leu Ala Pro Ser Ser
        130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
        195                 200                 205
Thr Tyr Ile Cys Asn Val Asn His Lys Pro Ser Asn Thr Lys Val Asp
        210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
        290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
        355                 360                 365
Glu Leu Thr Lys Asn Gln Val Ser Leu Thr Cys Leu Val Lys Gly Phe
        370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
Asn Val Phe Ser Cys Ser Val Met His Glu Ala Leu His Asn His Tyr
        435                 440                 445
Thr Gln Lys Ser Leu Ser Leu Ser Pro Gly Lys Gly Gly Gly Gly Ser
        450                 455                 460
Gly Gly Gly Gly Ser Gly Gly Gly Ser Gly Gly Gly Ser Glu
465                 470                 475                 480
Val Gln Leu Val Glu Ser Gly Gly Gly Leu Val Gln Pro Gly Gly Ser
```

```
                        485                 490                 495
Leu Arg Leu Ser Cys Ala Ala Ser Gly Tyr Thr Phe Thr Asn Tyr Gly
            500                 505                 510

Met Asn Trp Val Arg Gln Ala Pro Gly Lys Gly Leu Glu Trp Val Gly
            515                 520                 525

Trp Ile Asn Thr Tyr Thr Gly Glu Pro Thr Tyr Ala Ala Asp Phe Lys
            530                 535                 540

Arg Arg Phe Thr Phe Ser Leu Asp Thr Ser Lys Ser Thr Ala Tyr Leu
545                 550                 555                 560

Gln Met Asn Ser Leu Arg Ala Glu Asp Thr Ala Val Tyr Tyr Cys Ala
                565                 570                 575

Lys Tyr Pro His Tyr Tyr Gly Ser Ser His Trp Tyr Phe Asp Val Trp
                580                 585                 590

Gly Gln Gly Thr Leu Val Thr Val Ser Ala Ser Val Ala Ala Pro
                595                 600                 605

Ser Val Phe Ile Phe Pro Pro Ser Asp Glu Gln Leu Lys Ser Gly Thr
            610                 615                 620

Ala Ser Val Val Cys Leu Leu Asn Asn Phe Tyr Pro Arg Glu Ala Lys
625                 630                 635                 640

Val Gln Trp Lys Val Asp Asn Ala Leu Gln Ser Gly Asn Ser Gln Glu
                645                 650                 655

Ser Val Thr Glu Gln Asp Ser Lys Asp Ser Thr Tyr Ser Leu Ser Ser
            660                 665                 670

Thr Leu Thr Leu Ser Lys Ala Asp Tyr Glu Lys His Lys Val Tyr Ala
                675                 680                 685

Cys Glu Val Thr His Gln Gly Leu Ser Ser Pro Val Thr Lys Ser Phe
            690                 695                 700

Asn Arg Gly Glu Cys
705

<210> SEQ ID NO 2
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: <VEGF> VL-CH1 domains of modified Fab Fragment
      (CH1-CL exchange)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Ser Ser Ala Ser Thr
            100                 105                 110
```

```
Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys
    210

<210> SEQ ID NO 3
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Unmodified light chain <Ang-2>

<400> SEQUENCE: 3

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 4
<211> LENGTH: 709
```

<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Unmodified heavy chain <Ang-2> with N-terminal fused <VEGF> VH-CL domains of modified Fab Fragment (CH1-CL exchange)

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Gly Gly Gly Ser Gly Gly Gly Gly Gly Ser
225                 230                 235                 240

Gly Gly Gly Gly Ser Gly Gly Gly Ser Gln Val Gln Leu Val Glu
                245                 250                 255

Ser Gly Ala Glu Val Lys Lys Pro Gly Ala Ser Val Lys Val Ser Cys
            260                 265                 270

Lys Ala Ser Gly Tyr Thr Phe Thr Gly Tyr Tyr Met His Trp Val Arg
        275                 280                 285

Gln Ala Pro Gly Gln Gly Leu Glu Trp Met Gly Trp Ile Asn Pro Asn
    290                 295                 300

Ser Gly Gly Thr Asn Tyr Ala Gln Lys Phe Gln Gly Arg Val Thr Met
305                 310                 315                 320

Thr Arg Asp Thr Ser Ile Ser Thr Ala Tyr Met Glu Leu Ser Arg Leu
                325                 330                 335

Arg Ser Asp Asp Thr Ala Val Tyr Tyr Cys Ala Arg Ser Pro Asn Pro
            340                 345                 350

Tyr Tyr Tyr Asp Ser Ser Gly Tyr Tyr Tyr Pro Gly Ala Phe Asp Ile
```

```
                355                 360                 365
Trp Gly Gln Gly Thr Met Val Thr Val Ser Ala Ser Thr Lys Gly
            370                 375                 380
Pro Ser Val Phe Pro Leu Ala Pro Ser Ser Lys Ser Thr Ser Gly Gly
385                 390                 395                 400
Thr Ala Ala Leu Gly Cys Leu Val Lys Asp Tyr Phe Pro Glu Pro Val
                405                 410                 415
Thr Val Ser Trp Asn Ser Gly Ala Leu Thr Ser Gly Val His Thr Phe
            420                 425                 430
Pro Ala Val Leu Gln Ser Ser Gly Leu Tyr Ser Leu Ser Ser Val Val
                435                 440                 445
Thr Val Pro Ser Ser Ser Leu Gly Thr Gln Thr Tyr Ile Cys Asn Val
            450                 455                 460
Asn His Lys Pro Ser Asn Thr Lys Val Asp Lys Lys Val Glu Pro Lys
465                 470                 475                 480
Ser Cys Asp Lys Thr His Thr Cys Pro Pro Cys Pro Ala Pro Glu Leu
                485                 490                 495
Leu Gly Gly Pro Ser Val Phe Leu Phe Pro Pro Lys Pro Lys Asp Thr
            500                 505                 510
Leu Met Ile Ser Arg Thr Pro Glu Val Thr Cys Val Val Val Asp Val
                515                 520                 525
Ser His Glu Asp Pro Glu Val Lys Phe Asn Trp Tyr Val Asp Gly Val
530                 535                 540
Glu Val His Asn Ala Lys Thr Lys Pro Arg Glu Glu Gln Tyr Asn Ser
545                 550                 555                 560
Thr Tyr Arg Val Val Ser Val Leu Thr Val Leu His Gln Asp Trp Leu
                565                 570                 575
Asn Gly Lys Glu Tyr Lys Cys Lys Val Ser Asn Lys Ala Leu Pro Ala
            580                 585                 590
Pro Ile Glu Lys Thr Ile Ser Lys Ala Lys Gly Gln Pro Arg Glu Pro
            595                 600                 605
Gln Val Tyr Thr Leu Pro Pro Ser Arg Asp Glu Leu Thr Lys Asn Gln
610                 615                 620
Val Ser Leu Thr Cys Leu Val Lys Gly Phe Tyr Pro Ser Asp Ile Ala
625                 630                 635                 640
Val Glu Trp Glu Ser Asn Gly Gln Pro Glu Asn Asn Tyr Lys Thr Thr
                645                 650                 655
Pro Pro Val Leu Asp Ser Asp Gly Ser Phe Phe Leu Tyr Ser Lys Leu
            660                 665                 670
Thr Val Asp Lys Ser Arg Trp Gln Gln Gly Asn Val Phe Ser Cys Ser
            675                 680                 685
Val Met His Glu Ala Leu His Asn His Tyr Thr Gln Lys Ser Leu Ser
            690                 695                 700
Leu Ser Pro Gly Lys
705

<210> SEQ ID NO 5
<211> LENGTH: 709
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Modified heavy chain <VEGF> (CH1-CL exchange)
      with C-terminal fused <Ang-2> V Fragment

<400> SEQUENCE: 5

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400
```

```
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys Gly Gly Gly Ser Gly Gly
    450                 455                 460
Gly Gly Ser Gly Gly Gly Ser Gly Gly Gly Ser Gln Val Gln
465                 470                 475                 480
Leu Val Glu Ser Gly Ala Glu Val Lys Lys Pro Gly Ala Ser Val Lys
                485                 490                 495
Val Ser Cys Lys Ala Ser Gly Tyr Thr Phe Thr Gly Tyr Tyr Met His
            500                 505                 510
Trp Val Arg Gln Ala Pro Gly Gln Gly Leu Glu Trp Met Gly Trp Ile
        515                 520                 525
Asn Pro Asn Ser Gly Gly Thr Asn Tyr Ala Gln Lys Phe Gln Gly Arg
    530                 535                 540
Val Thr Met Thr Arg Asp Thr Ser Ile Ser Thr Ala Tyr Met Glu Leu
545                 550                 555                 560
Ser Arg Leu Arg Ser Asp Asp Thr Ala Val Tyr Tyr Cys Ala Arg Ser
                565                 570                 575
Pro Asn Pro Tyr Tyr Tyr Asp Ser Ser Gly Tyr Tyr Pro Gly Ala
            580                 585                 590
Phe Asp Ile Trp Gly Gln Gly Thr Met Val Thr Val Ser Ser Ala Ser
        595                 600                 605
Thr Lys Gly Pro Ser Val Phe Pro Leu Ala Pro Ser Ser Lys Ser Thr
    610                 615                 620
Ser Gly Gly Thr Ala Ala Leu Gly Cys Leu Val Lys Asp Tyr Phe Pro
625                 630                 635                 640
Glu Pro Val Thr Val Ser Trp Asn Ser Gly Ala Leu Thr Ser Gly Val
                645                 650                 655
His Thr Phe Pro Ala Val Leu Gln Ser Ser Gly Leu Tyr Ser Leu Ser
            660                 665                 670
Ser Val Val Thr Val Pro Ser Ser Ser Leu Gly Thr Gln Thr Tyr Ile
        675                 680                 685
Cys Asn Val Asn His Lys Pro Ser Asn Thr Lys Val Asp Lys Lys Val
    690                 695                 700
Glu Pro Lys Ser Cys
705

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This sequence may encompass 3, 4, 5, or 6
      repeating 'GGGS' units
<220> FEATURE:
<223> OTHER INFORMATION: see specification as filed for detailed
      description of substitutions and preferred embodiments

<400> SEQUENCE: 6
```

```
Gly Gly Gly Ser Gly Gly Gly Ser Gly Gly Gly Ser Gly Gly Gly Ser
1               5                   10                  15

Gly Gly Gly Ser Gly Gly Gly Ser
                20
```

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This region may encompass 3, 4, 5, or 6
      repeating 'GGGS' units
<220> FEATURE:
<221> NAME/KEY: misc_feature
<222> LOCATION: (24)..(27)
<223> OTHER INFORMATION: May or may not be present
<220> FEATURE:
<223> OTHER INFORMATION: see specification as filed for detailed
      description of substitutions and preferred embodiments

<400> SEQUENCE: 7

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly
                20                  25
```

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 2, 3, 4, or
      5 repeating 'GGGGS' units
<220> FEATURE:
<223> OTHER INFORMATION: see specification as filed for detailed
      description of substitutions and preferred embodiments

<400> SEQUENCE: 8

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
                20                  25
```

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This region may encompass 2, 3, 4, or 5
      repeating 'GGGGS' units
<220> FEATURE:
<221> NAME/KEY: misc_feature
<222> LOCATION: (26)..(28)
<223> OTHER INFORMATION: May or may not be present
<220> FEATURE:
<223> OTHER INFORMATION: see specification as filed for detailed -continued

```
description of substitutions and preferred embodiments

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly
            20                  25

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Gly Gly Gly Ser
1               5                   10

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly Ser Gly Gly Gly Gly Ser Gly
1               5                   10                  15

Gly Gly Gly Ser
            20
```

BISPECIFIC ANTIGEN BINDING PROTEINS

PRIORITY TO RELATED APPLICATION(S)

This application claims the benefit of European Patent Application No. 09007857 filed, Jun. 16, 2009, which is hereby incorporated by reference in its entirety.

The present invention relates to bispecific antigen binding proteins, methods for their production, pharmaceutical compositions containing said protein, and uses thereof.

SEQUENCE LISTING

The instant application contains a Sequence Listing which has been submitted via EFS-Web and is hereby incorporated by reference in its entirety. Said ASCII copy, created on Apr. 29, 2010, is named 26145.txt and is 26,572 bytes in size.

BACKGROUND OF THE INVENTION

Engineered proteins, such as bi- or multispecific antibodies capable of binding two or more antigens, are known in the art. Such multispecific binding proteins can be generated using cell fusion, chemical conjugation, or recombinant DNA techniques.

A wide variety of recombinant multispecific antibody formats have been developed in the recent past, e.g. tetravalent bispecific antibodies by fusion of, e.g. an IgG antibody format and single chain domains (see e.g. Coloma, M. J., et. al., Nature Biotech. 15 (1997) 159-163; WO 2001/077342; and Morrison, S. L., Nature Biotech. 25 (2007) 1233-1234.

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et. al., Nature Biotech 23 (2005) 1126-1136; Fischer, N., and Léger, O., Pathobiology 74 (2007) 3-14; Shen, J., et. al., J. Immunol. Methods 318 (2007) 65-74; Wu, C., et al., Nature Biotech 25 (2007) 1290-1297).

All such formats use linkers either to fuse the antibody core (IgA, IgD, IgE, IgG or IgM) to a further binding protein (e.g. scFv) or to fuse e.g. two Fab fragments or scFv (Fischer, N., and Léger, O., Pathobiology 74 (2007) 3-14). While it is obvious that linkers have advantages for the engineering of bispecific antibodies, they may also cause problems in therapeutic settings. Indeed, these foreign peptides might elicit an immune response against the linker itself or the junction between the protein and the linker. Further more, the flexible nature of these peptides makes them more prone to proteolytic cleavage, potentially leading to poor antibody stability, aggregation and increased immunogenicity. In addition one may want to retain effector functions, such as e.g. complement-dependent cytotoxicity (CDC) or antibody dependent cellular cytotoxicity (ADCC), which are mediated through the Fc part by maintaining a high degree of similarity to naturally occurring antibodies.

Thus ideally, one should aim at developing bispecific antibodies that are very similar in general structure to naturally occurring antibodies (like IgA, IgD, IgE, IgG or IgM) with minimal deviation from human sequences.

In one approach bispecific antibodies that are very similar to natural antibodies have been produced using the quadroma technology (see Milstein, C. and Cuello, A. C., Nature 305 (1983) 537-540) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibody species are generated of which only one is the desired, functional bispecific antibody. Due to the presence of mispaired byproducts, and significantly reduced production yields, means sophisticated purification procedures are required (see e.g. Morrison, S. L., Nature Biotech. 25 (2007) 1233-1234). In general the same problem of mispaired byproducts remains if recombinant expression techniques are used.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway, J. B., Protein Eng. 9 (1996) 617-621; and WO 96/027011). The percentage of heterodimer could be further increased by remodeling the interaction surfaces of the two CH3 domains using a phage display approach and the introduction of a disulfide bridge to stabilize the heterodimers (Merchant A. M, et al., Nature Biotech 16 (1998) 677-681; Atwell, S., et al., J. Mol. Biol. 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bispecific antibodies against two antigens starting from two antibodies against the first and the second antigen, as either the heavy chains of these antibodies an/or the identical light chains have to be optimized.

Another approach to circumvent the problem of mispaired byproducts in the preparation of bispecific antibodies, is to switch from heterodimers to homodimers by using an full length antibody which specifically binds to a first antigen and which has fused to its heavy chains N-termini two fused Fab fragments which specifically bind to a second antigen as described e.g. in WO2001/077342. One important disadvantage of this strategy is the formation of undesired inactive byproducts by the mispairing of the light chains of the full length antibody with the CH1-VH domains of the Fab fragments and by the mispairing of the Fab fragment light chains with CH1-VH domains of the full length antibody.

WO 2006/093794 relates to heterodimeric protein binding compositions. WO 99/37791 describes multipurpose antibody derivatives. Morrison, S., L., et al the J. Immunolog, 160 (1998) 2802-2808 refers to the influence of variable region domain exchange on the functional properties of IgG.

SUMMARY OF THE INVENTION

The invention comprises a bispecific antigen binding protein, comprising:
  a) two light chains and two heavy chains of an antibody that comprises two Fab fragments and that specifically binds to a first antigen; and b) two additional Fab fragments of an antibody which specifically binds to a second antigen, wherein the additional Fab fragments are both fused via a peptide connector either at the C- or N-termini of the heavy chains of a);
wherein the bispecific antigen binding protein also comprises a structural modification selected from the group consisting of:
i) in both Fab fragments of a) or in both Fab fragments of b)
the variable domains VL and VH are replaced by each other, and the constant domains CL and CH1 are replaced by each other, or the constant domains CL and CH1 are replaced by each other;
ii) in both Fab fragments of a)
the variable domains VL and VH are replaced by each other, and
the constant domains CL and CH1 are replaced by each other, and
in both Fab fragments of b)
the variable domains VL and VH are replaced by each other, or
the constant domains CL and CH1 are replaced by each other;
iii) in both Fab fragments of a)
the variable domains VL and VH are replaced by each other, or
the constant domains CL and CH1 are replaced by each other, and
in both Fab fragments of b)
the variable domains VL and VH are replaced by each other, and
the constant domains CL and CH1 are replaced by each other;
v) in both Fab fragments of a)
the variable domains VL and VH are replaced by each other, and
in both Fab fragments of b)
the constant domains CL and CH1 are replaced by each other; and
v) in both Fab fragments of a)
the constant domains CL and CH1 are replaced by each other, and in both Fab fragments of b)
the variable domains VL and VH are replaced by each other.

A further embodiment of the invention is a method for the preparation of an antigen binding protein according to the invention comprising the steps of
a) transforming a host cell with
vectors comprising nucleic acid molecules encoding a bispecific antigen binding protein according to the invention
b) culturing the host cell under conditions that allow synthesis of said antibody molecule; and
c) recovering said antibody molecule from said culture.

A further embodiment of the invention is a host cell comprising
vectors comprising nucleic acid molecules encoding an antigen binding protein according to the invention A further embodiment of the invention is a pharmaceutical composition comprising an antigen binding protein according to the invention and at least one pharmaceutically acceptable excipient.

A further embodiment of the invention is a method for the treatment of a patient in need of therapy, comprising administering to the patient a therapeutically effective amount of an antigen binding protein according to the invention.

According to the invention, the ratio of a desired bispecific antigen binding protein compared to undesired side products can be improved by the replacement of certain domains a) in the Fab fragment of the full length antibody which specifically binds to the a first antigen and/or b) in the two additional fused Fab fragments. In this way the undesired mispairing of the light chains with the wrong CH1-VH domains can be reduced.

BRIEF DESCRIPTION OF THE DRAWINGS

FIG. 4a shows bispecific antigen binding proteins. FIGS. 4b and 4c show all combination of VH/VL and/or CH1/CL domain exchanges within the full length Fab fragments and the additional Fab fragments which lead to bispecific antigen binding proteins according to the invention with reduced mispairing.

DETAILED DESCRIPTION OF THE INVENTION

Figure 1:
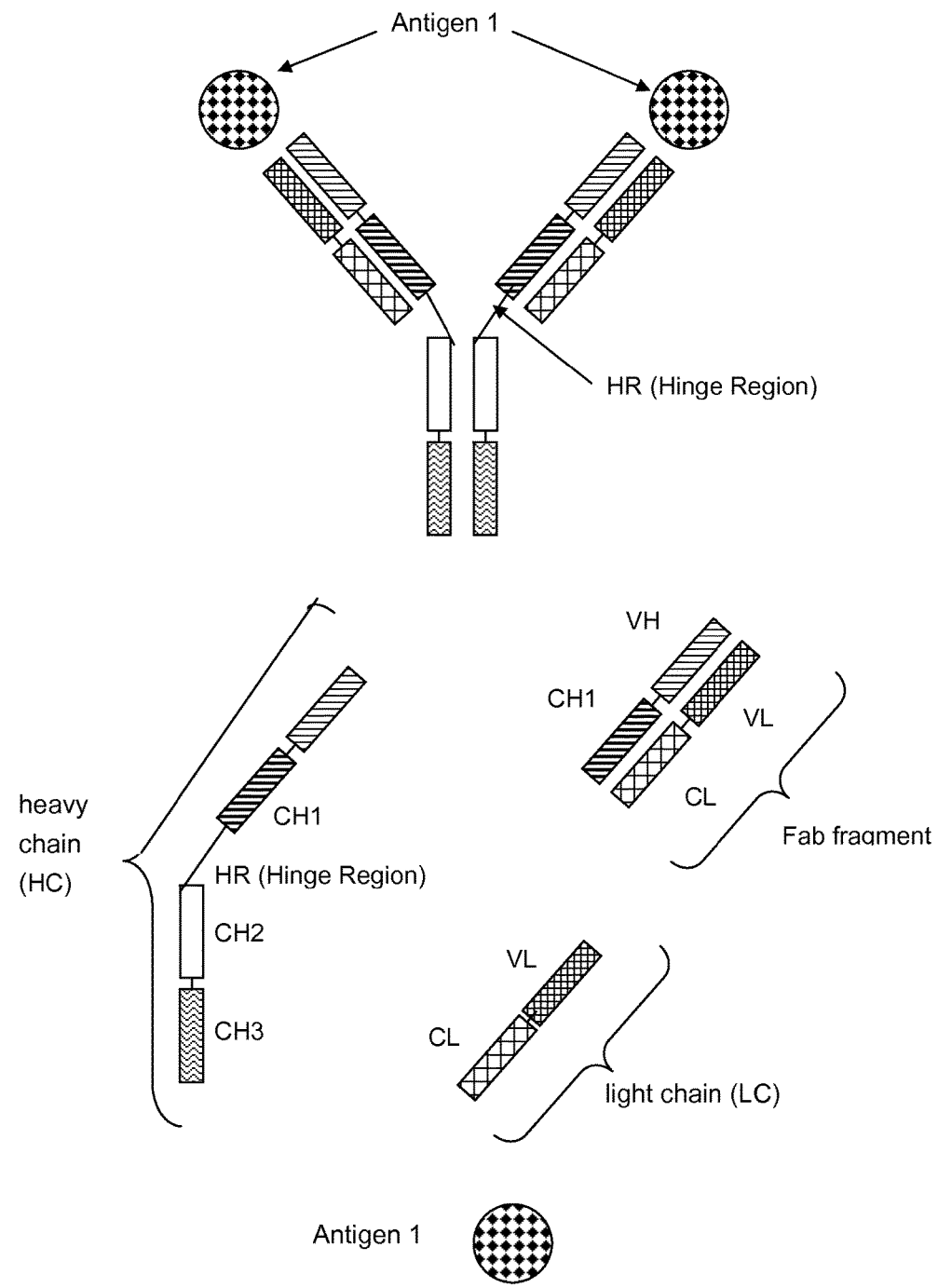
FIG. 1 Schematic structure of a full length antibody without CH4 domain specifically binding to a first antigen 1 with two pairs of heavy and light chain which comprise variable and constant domains in a typical order.

The invention comprises a bispecific antigen binding protein, comprising:
a) two light chains and two heavy chains of an antibody that comprises two Fab fragments and that specifically binds to a first antigen; and
b) two additional Fab fragments of an antibody which specifically binds to a second antigen, wherein the additional Fab fragments are both fused via a peptide connector either at the C- or N-termini of the heavy chains of a);
wherein the bispecific antigen binding protein also comprises a structural modification selected from the group consisting of:
i) in both Fab fragments of a) or in both Fab fragments of b)
the variable domains VL and VH are replaced by each other, and the constant domains CL and CH1 are replaced by each other, or the constant domains CL and CH1 are replaced by each other;
ii) in both Fab fragments of a)
the variable domains VL and VH are replaced by each other, and
the constant domains CL and CH1 are replaced by each other, and
in both Fab fragments of b)
the variable domains VL and VH are replaced by each other, or
the constant domains CL and CH1 are replaced by each other;
iii) in both Fab fragments of a)
the variable domains VL and VH are replaced by each other, or
the constant domains CL and CH1 are replaced by each other, and
in both Fab fragments of b)
the variable domains VL and VH are replaced by each other, and
the constant domains CL and CH1 are replaced by each other;
v) in both Fab fragments of a)
the variable domains VL and VH are replaced by each other, and
in both Fab fragments of b)
the constant domains CL and CH1 are replaced by each other; and
v) in both Fab fragments of a)
the constant domains CL and CH1 are replaced by each other, and
in both Fab fragments of b)
the variable domains VL and VH are replaced by each other.

One embodiment of the invention is the bispecific antigen binding protein according to the invention wherein
the additional Fab fragments are fused both via a peptide connector either to the C-termini of the heavy chains of a), or to the N-termini of the heavy chains of a).

Another embodiment of the invention is the bispecific antigen binding protein according to the invention wherein
the additional Fab fragments are fused both via a peptide connector either to the C-termini of the heavy chains of a).

Another embodiment of the invention is the bispecific antigen binding protein according to the invention wherein
the additional Fab fragments are fused both via a peptide connector to the N-termini of the heavy chains of a).

Another embodiment of the invention is the bispecific antigen binding protein according to the invention wherein the bispecific antigen binding protein also comprises a structural modification selected from the group consisting of:
i) in both Fab fragments of a), or in both Fab fragments of b),
the variable domains VL and VH are replaced by each other, and/or
the constant domains CL and CH1 are replaced by each other.

Another embodiment of the invention is the bispecific antigen binding protein according to the invention comprising the following structural modifications:
i) in both Fab fragments of a)
the variable domains VL and VH are replaced by each other, and/or
the constant domains CL and CH1 are replaced by each other.

Another embodiment of the invention is the bispecific antigen binding protein according to the invention comprising the following structural modifications:
i) in both Fab fragments of a)
the constant domains CL and CH1 are replaced by each other.

Another embodiment of the invention is the bispecific antigen binding protein according to the invention comprising the following structural modifications:
i) in both Fab fragments of b)
the variable domains VL and VH are replaced by each other, and/or
the constant domains CL and CH1 are replaced by each other.

Another embodiment of the invention is the bispecific antigen binding protein according to the invention comprising the following structural modifications
i) in both Fab fragments of b)
the constant domains CL and CH1 are replaced by each other.

Figure 3A:
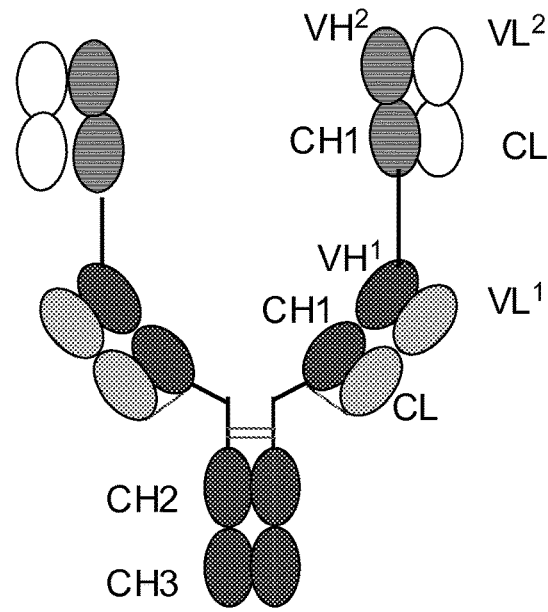
FIG. 3 Schematic structure of a full length antibody specifically binding to a first antigen 1 which has fused to the N-terminus of its heavy chain two unmodified Fab fragments specifically binding to a second antigen 2 (FIG. 3a) and the undesired side products due to mispairing (FIG. 3b and FIG. 3c).
Figure 3B:
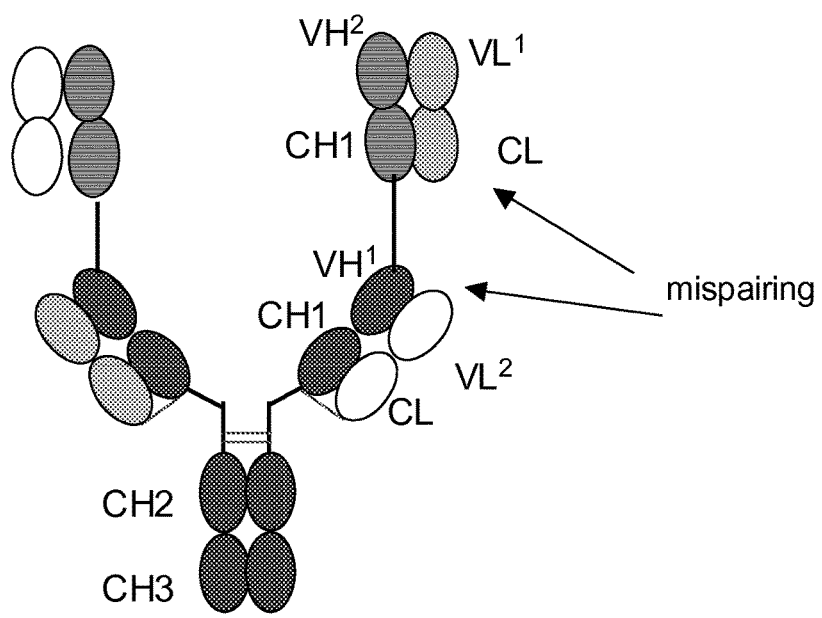
Figure 3C:
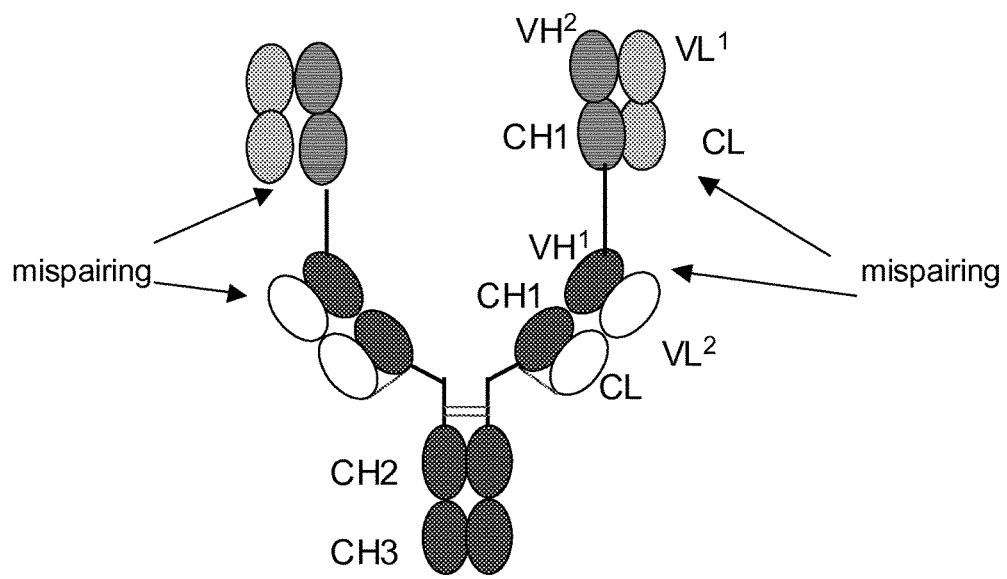
Figure 4A:
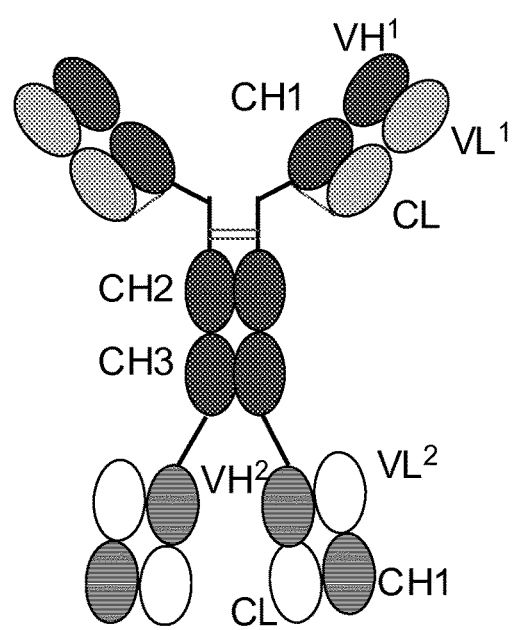
FIGS. 4a, 4b and 4c Schematic structure of a bispecific antigen binding proteins according to the invention in which the mispairing is reduced by the replacement of certain domains a) in the Fab fragment of the full length antibody which specifically binds to a first antigen 1 and/or b) in the two additional fused Fab fragments antibody which specifically binds to a second antigen 2.
Figure 4B:
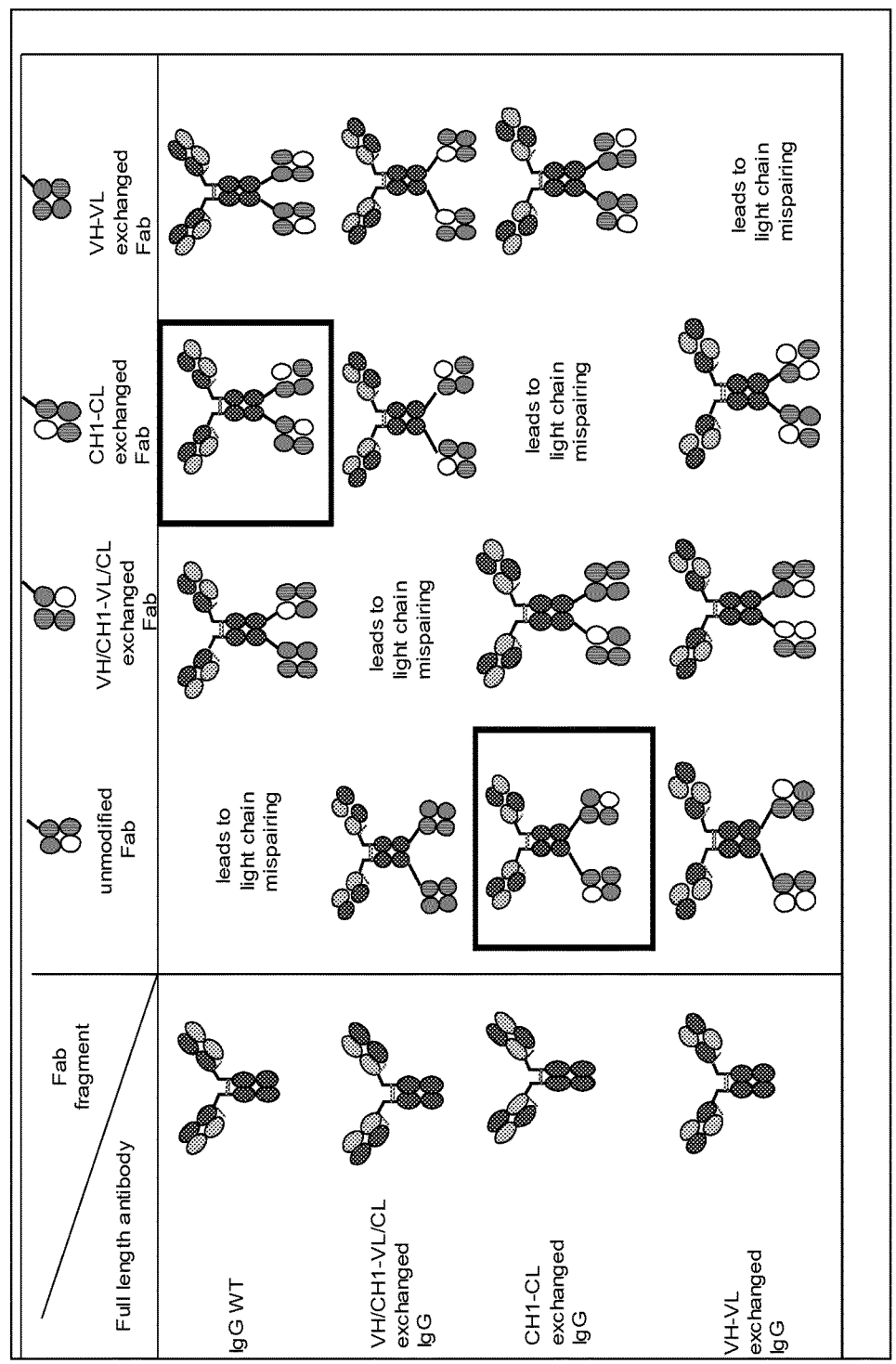
Figure 4C:
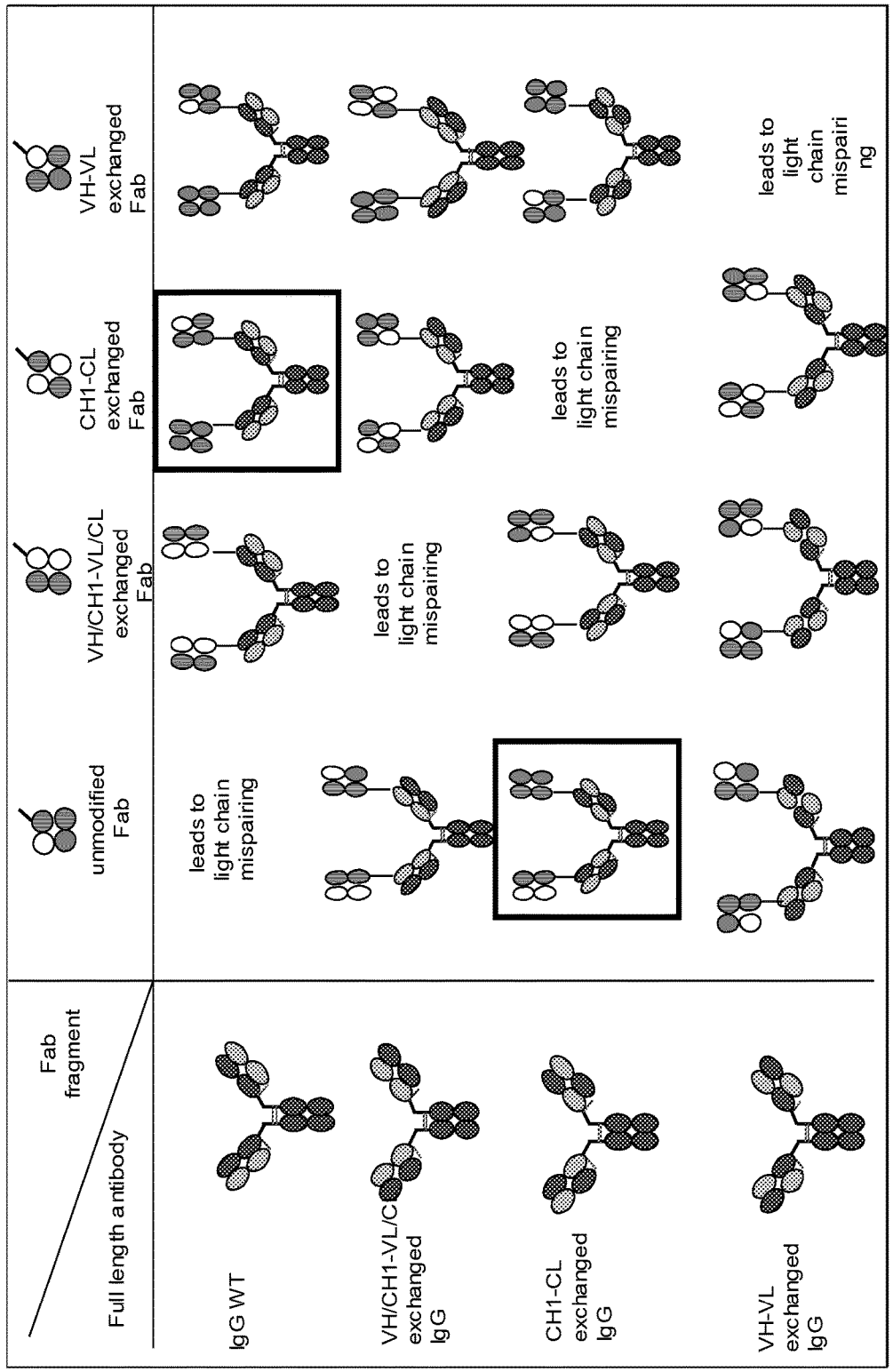

According to the invention, the ratio of a desired bispecific antigen binding protein compared to undesired side products (due to mispairing of the light chains with the wrong CH1-VH domains) can be reduced by the replacement of certain domains a) in the Fab fragment of the full length antibody which specifically binds to the a first antigen and/or b) in the two additional fused Fab fragments. Mispairing in this connection means the association of i) the light chain of the full length antibody under a) with CH1-VH domains of the Fab fragments under b); or ii) the light chain of the Fab fragments under b) with the CH1-VH domains of the full length antibody under a) (see FIG. 3) which leads to undesired inactive or not fully functional byproducts.

Figure 2A:
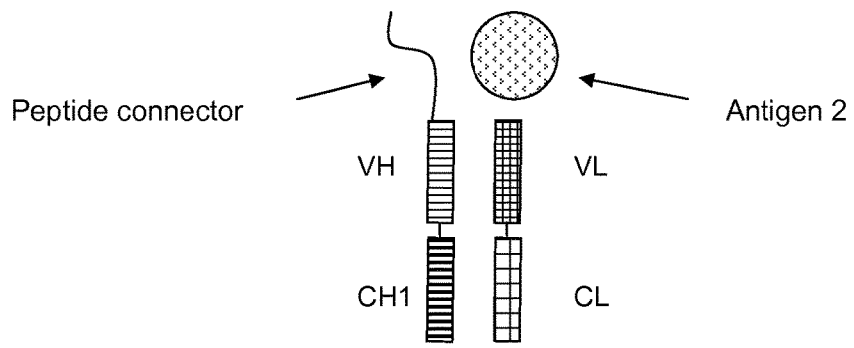
FIGS. 2a and 2b Schematic structure of typical unmodified Fab fragments specifically binding to a second antigen 2 with the peptide connector either at the C-terminus (FIG. 2a) or N-terminus (FIG. 2b) of the CH1-VH chain.
Figure 2B:
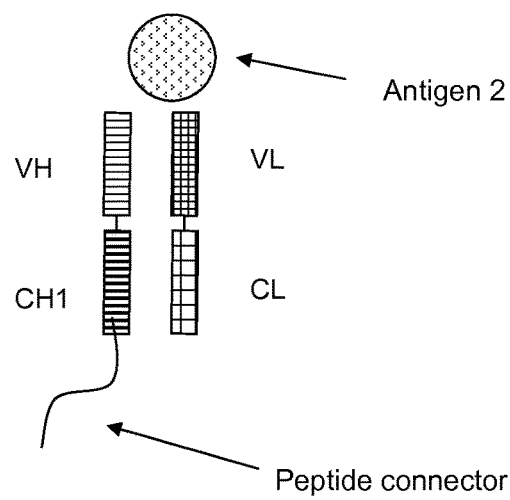

The term "antibody" as used herein denotes a full length antibody consisting of two antibody heavy chains and two antibody light chains (see FIG. 1). A heavy chain of full length antibody is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the heavy chain of full length antibody is a polypeptide consisting in N-terminal to C-terminal direction of VH, CHL HR, CH2 and CH3. The light chain of full length antibody is a polypeptide consisting in N-terminal to C-terminal direction of an antibody light chain variable domain (VL), and an antibody light chain constant domain (CL), abbreviated as VL-CL. The antibody light chain constant domain (CL) can be Λ (kappa) or λ (lambda). The antibody chains are linked together via inter-polypeptide disulfide bonds between the CL domain and the CH1 domain (i.e. between the light and heavy chain) and between the hinge regions of the full length antibody heavy chains. Examples of typical full length antibodies are natural antibodies like IgG (e.g. IgG 1 and IgG2), IgM, IgA, IgD, and IgE.) The antibodies according to the invention can be from a single species e.g. human, or they can be chimerized or humanized antibodies. The full length antibodies according to the invention comprise two antigen binding sites each formed by a pair of VH and VL, which both specifically bind to the same (first) antigen. The C-terminus of the heavy or light chain of the full length antibody denotes the last amino acid at the C-terminus of the heavy or light chain. The antibody comprises two identical Fab fragments consisting of the VH and CH1 domain of the heavy chain and the VL and CL domain of the light chain. (see FIGS. 1 and 2).

An "additional Fab fragment" (see FIG. 2) of an antibody which specifically binds to a second antigen refers to a further Fab fragment consisting of the VH and CH1 domain of the heavy chain and the VL and CL domain of the light chain of the second antibody. The additional Fab fragments are fused in their unmodified form (see FIG. 3) via the heavy chain part (either CH1 or VH domain) to the C- or N-termini of the heavy chains or light chains of the antibody specifically binding to a first antigen.

The term "peptide connector" as used within the invention denotes a peptide with amino acid sequences, which is preferably of synthetic origin. These peptide connectors according to invention are used to fuse the antigen binding peptides to the C- or N-terminus of the full length and/or modified full length antibody chains to form a bispecific antigen binding protein according to the invention. Preferably the peptide connectors under c) are peptides with an amino acid sequence with a length of at least 5 amino acids, preferably with a length of 5 to 100, more preferably of 10 to 50 amino acids. In one embodiment the peptide connector is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment the peptide connector is $(G_4S)_2$.

The terms "binding site" or "antigen-binding site" as used herein denotes the region(s) of an antigen binding protein according to the invention to which a ligand (e.g. the antigen or antigen fragment of it) actually binds and which is derived from an antibody molecule or a fragment thereof (e.g. a Fab fragment). The antigen-binding site according to the invention comprises an antibody heavy chain variable domains (VH) and an antibody light chain variable domains (VL).

The antigen-binding sites (i. the pairs of VH/VL) that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of an antigen binding protein of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody or antigen binding protein for a particular epitope of an antigen. Natural antibodies, for example, are monospecific. Bispecific antibodies are antibodies which have two different antigen-binding specificities. Where an antibody has more than one specificity, the recognized epitopes may be associated with a single antigen or with more than one antigen.

The term "monospecific" antibody or antigen binding protein as used herein denotes an antibody or antigen binding protein that has one or more binding sites each of which bind to the same epitope of the same antigen.

The term "valent" as used within the current application denotes the presence of a specified number of binding sites in an antibody molecule. A natural antibody for example or a full length antibody according to the invention has two binding sites and is bivalent. The term "tetravalent", denotes the presence of four binding sites in an antigen binding protein. The term "tetravalent, bispecific" as used herein denotes antigen binding protein according to the invention that has four antigen-binding sites of which two binds to another antigen (or another epitope of the antigen). Antigen binding proteins of the present invention have four binding sites and are tetravalent.

The full length antibodies of the invention comprise immunoglobulin constant regions of one or more immunoglobulin classes Immunoglobulin classes include IgG, IgM, IgA, IgD, and IgE isotypes and, in the case of IgG and IgA, their subtypes. In a preferred embodiment, an full length antibody of the invention has a constant domain structure of an IgG type antibody.

The terms "monoclonal antibody" or "monoclonal antibody composition" as used herein refer to a preparation of antibody or antibody or antigen binding protein molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S., L., et al., Proc. Natl. Acad. Sci. USA 81 (1984) 6851-6855; U.S. Pat. No. 5,202, 238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1 binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, S., P., C., et al., Monoclonal Antibodies and Cancer Therapy, Alan R. Liss (1985) 77-96; and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1 binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody (or antibody or antigen binding protein) from the antibody/antigen complex), $\lambda_D$ (dissociation constant), and $K_D$ ($k_D$/ka). Binding or specifically binding means a binding affinity ($K_D$) of $10^{-8}$ mol/l or less, preferably $10^{-9}$ M to $10^{-13}$ mol/l. Thus, a bispecific antigen binding protein according to the invention is specifically binding to each antigen for which it is specific with a binding affinity ($K_D$) of $10^{-8}$ mol/l or less, preferably $10^{-9}$ M to $10^{-13}$ mol/l.

Binding of the antibody to the FcγRIII can be investigated by a BIAcore assay (GE-Healthcare Uppsala, Sweden). The affinity of the binding is defined by the terms ka (rate constant for the association of the antibody from the antibody/antigen complex), $k_D$ (dissociation constant), and $K_D$ ($k_D$/ka).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is the to specifically bind an antigen when it preferentially recognizes its target antigen in a complex mixture of proteins and/or macromolecules.

In a further embodiment the bispecific antigen binding protein according to the invention is characterized in that the full length antibody is of human IgG1 subclass, or of human IgG1 subclass with the mutations L234A and L235A.

In a further embodiment the bispecific antigen binding protein according to the invention is characterized in that the full length antibody is of human IgG2 subclass.

In a further embodiment the bispecific antigen binding protein according to the invention is characterized in that the full length antibody is of human IgG3 subclass.

In a further embodiment the bispecific antigen binding protein according to the invention is characterized in that the full length antibody is of human IgG4 subclass or, of human IgG4 subclass with the additional mutation S228P.

Preferably the bispecific antigen binding protein according to the invention is characterized in that the full length antibody is of human IgG1 subclass, of human IgG4 subclass with the additional mutation S228P.

It has now been found that the bispecific antigen binding proteins according to the invention have improved characteristics such as biological or pharmacological activity, pharmacokinetic properties or toxicity. They can be used e.g. for the treatment of diseases such as cancer.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antigen binding protein according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1 to the constant region of most IgG antibody subclasses. Binding of C1 to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J., J., Mol. Immunol. 16 (1979) 907-917; Burton, D. R., et al., Nature 288 (1980) 338-344; Thommesen, J., E., et al., Mol. Immunol. 37 (2000) 995-1004; Idusogie, E., E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antigen binding protein according to the invention in the presence of effector cells. ADCC is measured preferably by the treatment of a preparation of antigen expressing cells with an antigen binding protein according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1 to the Fc part of most IgG antibody subclasses. Binding of C1 to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1 and C3 binding, whereas IgG4 does not activate the complement system and does not bind C1 and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M., R., et al., Glycobiology 5 (1995) 813-822; Jefferis, R., et al., Immunol. Rev. 163 (1998) 59-76; Wright, A., and Morrison, S., L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1 (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R., L., et al., J. Biol. Chem. 276 (2001) 6591-6604; Shields, R., L., et al., J. Biol. Chem. 277 (2002) 26733-26740; Simmons, L., C., et al., J. Immunol. Methods 263 (2002) 133-147).

Methods to enhance cell-mediated effector functions of monoclonal antibodies are reported e.g. in WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835, WO 2000/061739.

In one preferred embodiment of the invention, the bispecific antigen binding protein is glycosylated (if it comprises an Fc part of IgG1, IgG2, IgG3 or IgG4 subclass, preferably of IgG1 or IgG3 subclass) with a sugar chain at Asn297 whereby the amount of fucose within the sugar chain is 65% or lower (Numbering according to Kabat). In another embodiment is the amount of fucose within the sugar chain is between 5% and 65%, preferably between 20% and 40%. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antigen binding protein according to the invention the IgG subclass is of human IgG1 subclass, of human IgG1 subclass with the mutations L234A and L235A or of IgG3 subclass. In a further embodiment the amount of N-glycolylneuraminic acid (NGNA) is 1% or less and/or the amount of N-terminal alpha-1,3-galactose is 1% or less within the sugar chain. The sugar chain show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, Md. (1991), and by Brueggemann, M., et al., J. Exp. Med. 166 (1987) 1351-1361; Love, T., W., et al., Methods Enzymol. 178 (1989) 515-527. These structures are designated as G0, G1 ($\alpha$-1,6- or $\alpha$-1,3-), or G2 glycan residues, depending from the amount of terminal Gal residues (Raju, T., S., Bioprocess Int. 1 (2003) 44-53). CHO type glycosylation of antibody Fc parts is e.g. described by Routier, F., H., Glycoconjugate J. 14 (1997) 201-207. Antibodies which are recombinantly expressed in non-glyco-modified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of the sugar within the sugar chain at Asn297, related to the sum of all glycostructures attached to Asn297 (e.g. complex, hybrid and high mannose structures) measured by MALDI-TOF mass spectrometry and calculated as average value. The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antigen binding protein according to the invention is produced by recombinant means. Thus, one aspect of the current invention is a nucleic acid encoding the antigen binding protein according to the invention and a further aspect is a cell comprising the nucleic acid encoding an antigen binding protein according to the invention. Methods for recombinant production are widely known in the state of the art and comprise protein expression in prokaryotic and eukaryotic cells with subsequent isolation of the antigen binding protein and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antigen binding protein is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The bispecific antigen binding proteins according to the invention are suitably separated from the culture medium by conventional immunoglobulin purification procedures such as, for example, protein A-Sepharose, hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antigen binding protein are prepared by introducing appropriate nucleotide changes into the antigen binding protein DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence.

For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)— and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical composition comprising an antigen binding protein according to the invention. Another aspect of the invention is the use of an antigen binding protein according to the invention for the manufacture of a pharmaceutical composition. A further aspect of the invention is a method for the manufacture of a pharmaceutical composition comprising an antigen binding protein according to the invention. In another aspect, the present invention provides a composition, e.g. a pharmaceutical composition, containing an antigen binding protein according to the present invention, formulated together with a pharmaceutical carrier.

Another aspect of the invention is the pharmaceutical composition for the treatment of cancer.

Another aspect of the invention is the bispecific antigen binding protein according to the invention for the treatment of cancer.

Another aspect of the invention is the use of an antigen binding protein according to the invention for the manufacture of a medicament for the treatment of cancer.

Another aspect of the invention is a method of treatment of a patient suffering from cancer by administering an antigen binding protein according to the invention to the patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F., L., and Van der Eb, A., J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S., N., et al, PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO:1 unmodified heavy chain <Ang-2> with C-terminal fused <VEGF> VH-CL domains of modified Fab Fragment (CH1-CL exchange)
SEQ ID NO:2 <VEGF> VL-CH1 domains of modified Fab Fragment (CH1-CL exchange)
SEQ ID NO:3 unmodified light chain <Ang-2>
SEQ ID NO:4 unmodified heavy chain <Ang-2> with N-terminal fused <VEGF> VH-CL domains of modified Fab Fragment (CH1-CL exchange)
SEQ ID NO:5 modified heavy chain <VEGF> (CH1-CL exchange) with C-terminal fused <Ang-2>VH-CH1 domains of unmodified Fab Fragment

EXAMPLES

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991) Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods are used to manipulate DNA as described in Sambrook, J. et al., Molecular cloning: A laboratory manual; Cold Spring Harbor Laboratory Press, Cold Spring Harbor, N.Y., 1989. The molecular biological reagents are used according to the manufacturer's instructions.

Gene Synthesis

Desired gene segments are prepared from oligonucleotides made by chemical synthesis. The gene segments, which are flanked by singular restriction endonuclease cleavage sites, are assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments are confirmed by DNA sequencing. Gene synthesis fragments are ordered according to given specifications at Geneart (Regensburg, Germany).

DNA Sequence Determination

DNA sequences are determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 is used for sequence creation, mapping, analysis, annotation and illustration.

Expression Vectors

For the expression of the described bispecific tetravalent antibodies variants of expression plasmids for transient expression (e.g. in HEK293 EBNA or HEK293-F) cells based either on a cDNA organization with or without a CMV-Intron A promoter or on a genomic organization with a CMV promoter are applied.

Beside the antibody expression cassette the vectors contained:
- an origin of replication which allows replication of this plasmid in E. coli, and
- a β-lactamase gene which confers ampicillin resistance in E. coli.

The transcription unit of the antibody gene is composed of the following elements:
- unique restriction site(s) at the 5' end
- the immediate early enhancer and promoter from the human cytomegalovirus,
- followed by the Intron A sequence in the case of the cDNA organization,
- a 5'-untranslated region of a human antibody gene,
- a immunoglobulin heavy chain signal sequence,
- the human bispecific tetravalent antibody chain (wildtype or with domain exchange) either as cDNA or as genomic organization with an the immunoglobulin exon-intron organization
- a 3' untranslated region with a polyadenylation signal sequence, and
- unique restriction site(s) at the 3' end.

The fusion genes comprising the described antibody chains as described below are generated by PCR and/or gene synthesis and assembled with known recombinant methods and techniques by connection of the according nucleic acid segments e.g. using unique restriction sites in the respective vectors. The subcloned nucleic acid sequences are verified by DNA sequencing. For transient transfections larger quantities of the plasmids are prepared by plasmid preparation from transformed E. coli cultures (Nucleobond A X, Macherey-Nagel).

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Bispecific tetravalent antibodies are expressed by transient co-transfection of the respective three expression plasmids in adherently growing HEK293-EBNA or in HEK29-F cells growing in suspension as described below.

Transient Transfections in HEK293-EBNA System

Bispecific tetravalent antibodies are expressed by transient co-transfection of the respective three expression plasmids (e.g. encoding the modified heavy chain, as well as the corresponding light and modified light chain) in adherently growing HEK293-EBNA cells (human embryonic kidney cell line 293 expressing Epstein-Barr-Virus nuclear antigen; American type culture collection deposit number ATCC # CRL-10852, Lot. 959 218) cultivated in DMEM (Dulbecco's modified Eagle's medium, Gibco) supplemented with 10% Ultra Low IgG FCS (fetal calf serum, Gibco), 2 mM L-Glutamine (Gibco), and 250 µg/mL Geneticin (Gibco). For transfection FuGENE™ 6 Transfection Reagent (Roche Molecular Biochemicals) is used in a ratio of FuGENE™ reagent (µl) to DNA (µg) of 4:1 (ranging from 3:1 to 6:1). Proteins are expressed from the respective plasmids using a molar ratio of (modified and wildtype) light chain and modified heavy chain encoding plasmids of 1:1:1 (equimolar) ranging from 1:1:2 to 2:2:1, respectively. Cells are feeded at day 3 with L-Glutamine ad 4 mM, Glucose [Sigma] and NAA [Gibco]. Bispecific tetravalent antibody containing cell culture supernatants are harvested from day 5 to 11 after transfection by centrifugation and stored at −20° C. General information regarding the recombinant expression of human immunoglobulins in e.g. HEK293 cells is given in: Meissner, P. et al., Biotechnol. Bioeng. 75 (2001) 197-203.

Transient Transfections in HEK293-F System

Alternatively, bispecific tetravalent antibodies are generated by transient transfection of the respective plasmids (e.g. encoding the modified heavy chain, as well as the corresponding light and modified light chain) using the HEK293-F system (Invitrogen) according to the manufacturer's instruction. Briefly, HEK293-F cells (Invitrogen) growing in suspension either in a shake flask or in a stirred fermenter in serum free FreeStyle 293 expression medium (Invitrogen) are transfected with a mix of the three expression plasmids as described above and 293fectin or fectin (Invitrogen). For 2 L shake flask (Corning) HEK293-F cells are seeded at a density of 1.0E*6 cells/mL in 600 mL and incubated at 120 rpm, 8% CO2. The day after the cells are transfected at a cell density of ca. 1.5E*6 cells/mL with ca. 42 mL mix of A) 20 mL Opti-MEM (Invitrogen) with 600 µg total plasmid DNA (1 µg/mL) encoding the modified heavy chain, the corresponding light chain and the corresponding modified light chain in an equimolar ratio and B) 20 mL Opti-MEM+1.2 mL 293 fectin or fectin (2 µl/mL). According to the glucose consumption glucose solution is added during the course of the fermentation. The supernatant containing the secreted antibody is harvested after 5-10 days and antibodies are either directly purified from the supernatant or the supernatant is frozen and stored.

Protein Determination

The protein concentration of purified bispecific tetravalent antibodies and derivatives is determined by determining the optical density (OD) at 280 nm, using the molar extinction coefficient calculated on the basis of the amino acid sequence according to Pace, C., N., et al., Protein Science 4 (1995) 2411-1423.

Antibody Concentration Determination in Supernatants

The concentration of bispecific tetravalent antibodies in cell culture supernatants is estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2×PBS, Roche) and briefly four times with 0.5 mL 100 mM Na-citrate pH 5,0. Bound antibody is eluted by addition of 35 µl NuPAGE® LDS Sample Buffer (Invitrogen). Half of the sample is combined with NuPAGE® Sample Reducing Agent or left unreduced, respectively, and heated for 10 min at 70° C. Consequently, 5-30 µl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of bispecific tetravalent antibodies in cell culture supernatants is quantitatively measured by affinity HPLC chromatography. Briefly, cell culture supernatants containing antibodies and derivatives that bind to Protein A are applied to an Applied Biosystems Poros A/20 column in 200 mM KH2PO4, 100 mM sodium citrate, pH 7.4 and eluted from the matrix with 200 mM NaCl, 100 mM citric acid, pH 2,5 on an Agilent HPLC 1100 system. The eluted protein is quantified by UV absorbance and integration of peak areas. A purified standard IgG1 antibody served as a standard.

Alternatively, the concentration of bispecific tetravalent antibodies in cell culture supernatants is measured by Sandwich-IgG-ELISA. Briefly, StreptaWell High Bind Strepatavidin A-96 well microtiter plates (Roche) are coated with 100 µL/well biotinylated anti-human IgG capture molecule F(ab')2<h-Fcγ> BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants is added to the wells and incubated for 1-2 h on a microtiterplate shaker at room temperature. The wells are washed three times with 200 µL/well PBST and bound antibody is detected with 100 µl F(ab')2<hFcγ>POD (Dianova) at 0.1 µg/mL as detection antibody for 1-2 h on a microtiterplate shaker at room temperature. Unbound detection antibody is washed away three times with 200 µL/well PBST and the bound detection antibody is detected by addition of 100 µL ABTS/well. Determination of absorbance is performed on a Tecan Fluor Spectrometer at a measurement wavelength of 405 nm (reference wavelength 492 nm).

Protein Purification

Proteins are purified from filtered cell culture supernatants referring to standard protocols. In brief, bispecific tetravalent antibodies are applied to a Protein A Sepharose column (GE healthcare) and washed with PBS. Elution of bispecific tetravalent antibodies is achieved at pH 2.8 followed by immediate neutralization of the sample. Aggregated protein is separated from monomeric antibodies by size exclusion chromatography (Superdex 200, GE Healthcare) in PBS or in 20 mM Histidine, 150 mM NaCl pH 6.0. Monomeric fractions are pooled, concentrated if required using e.g. a MILLIPORE Amicon Ultra (30 MWCO) centrifugal concentrator, frozen and stored at −20° C. or −80° C. Part of the samples are provided for subsequent protein analytics and analytical characterization e.g. by SDS-PAGE, size exclusion chromatography or mass spectrometry.

SDS-PAGE

The NuPAGE® Pre-Cast gel system (Invitrogen) is used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer is used.

Analytical Size Exclusion Chromatography

Size exclusion chromatography for the determination of the aggregation and oligomeric state of bispecific tetravalent antibodies is performed by HPLC chromatography. Briefly, Protein A purified antibodies are applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2×PBS on a Dionex HPLC-System. The eluted protein is quantified by UV absorbance and integration of peak areas. BioRad Gel Filtration Standard 151-1901 served as a standard.

Mass Spectrometry

The total deglycosylated mass of the bispecific tetravalent antibodies is determined and confirmed via electrospray ionization mass spectrometry (ESI-MS). Briefly, 100 µg purified antibodies are deglycosylated with 50 mU N-Glycosidase F (PNGaseF, ProZyme) in 100 mM KH2PO4/K2HPO4, pH 7 at 37° C. for 12-24 h at a protein concentration of up to 2 mg/mL and subsequently desalted via HPLC on a Sephadex G25 column (GE Healthcare). The mass of the respective modified heavy, light chain and modified light chain is determined by ESI-MS after deglycosylation and reduction. In brief, 50 µl bispecific tetravalent antibody in 115 µl are incubated with 60 µl 1M TCEP and 50 µl 8 M Guanidine-hydrochloride subsequently desalted. The total mass and the mass of the reduced heavy and light chains is determined via ESI-MS on a Q-Star Elite MS system equipped with a NanoMate source.

VEGF Binding ELISA

The binding properties of the bispecific tetravalent antibodies is evaluated in an ELISA assay with full-length VEGF165-His protein (R&D Systems). For this sake Falcon polystyrene clear enhanced microtiter plates are coated with 100 µl 2 µg/mL recombinant human VEGF165 (R&D Systems) in PBS for 2 h at room temperature or over night at 4° C. The wells are washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series of the purified bispecific tetravalent antibodies in PBS (Sigma) is added to the wells and incubated for 1 h on a microtiterplate shaker at room temperature. The wells are washed three times with 300 µl PBST (0.2% Tween 20) and bound antibody is detected with 100 µL/well 0.1 µg/mL F(ab') <hFcgamma>POD (Immuno research) in 2% BSA 0.1% Tween 20 as detection antibody for 1 h on a microtiterplate shaker at room temperature. Unbound detection antibody is washed away three times with 300 µL/well PBST and the bound detection antibody is detected by addition of 100 µL ABTS/well. Determination of absorbance is performed on a Tecan Fluor Spectrometer at a measurement wavelength of 405 nm (reference wavelength 492 nm).

VEGF Binding: Kinetic Characterization of VEGF Binding at 37° C. by Surface Plasmon Resonance (Biacore)

In order to further corroborate the ELISA findings the binding of the bispecific tetravalent antibodies to VEGF is quantitatively analyzed using surface plasmon resonance technology on a Biacore T100 instrument according to the following protocol and analyzed using the T100 software package: Briefly, bispecific tetravalent antibodies are captured on a CM5-Chip via binding to a Goat Anti Human IgG (JIR 109-005-098). The capture antibody is immobilized by amino coupling using standard amino coupling as follows: HBS-N buffer served as running buffer, activation is done by mixture of EDC/NHS with the aim for a ligand density of 700 RU. The Capture-Antibody is diluted in coupling buffer NaAc, pH 5.0, c=2 µg/mL, finally still activated carboxyl groups are blocked by injection of 1 M Ethanolamine Capturing of bispecific tetravalent <VEGF> antibodies is done at a flow of 5 µL/min and c=10 nM, diluted with running buffer+1 mg/mL BSA; a capture level of approx. 30 RU should be reached. rhVEGF (rhVEGF, R&D-Systems Cat.-No, 293-VE) is used as analyte. The kinetic characterization of VEGF binding to bispecific tetravalent <VEGF> antibodies is performed at 25° C. or 37° C. in PBS+0.005% (v/v) Tween20 as running buffer. The sample is injected with a flow of 50 µL/min and an association of time 80 sec. and a dissociation time of 1200 sec with a concentration series of rhVEGF from 300-0.29 nM. Regeneration of free capture antibody surface is performed with 10 mM Glycin pH 1.5 and a contact time of 60 sec after each analyte cycle. Kinetic constants are calculated by using the usual double referencing method (control reference: binding of rhVEGF to capture molecule Goat Anti Human IgG, blanks on the measuring flow cell, rhVEGF concentration "0", Model: Langmuir binding 1:1, (Rmax set to local because of capture molecule binding).

Ang-2 Binding ELISA

The binding properties of the bispecific tetravalent antibodies is evaluated in an ELISA assay with full-length Ang-2-His protein (R&D Systems). For this sake Falcon polystyrene clear enhanced microtiter plates are coated with 100 µl 1 µg/mL recombinant human Ang-2 (R&D Systems, carrier-free) in PBS for 2 h at room temperature or over night at 4° C. The wells are washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series of the purified bispecific tetravalent antibodies in PBS (Sigma) is added to the wells and incubated for 1 h on a microtiterplate shaker at room temperature. The wells are washed three times with 300 µl PBST (0.2% Tween 20) and bound antibody is detected with 100 µL/well 0.1 µg/mL F(ab') <hk>POD (Biozol Cat.No. 206005) in 2% BSA 0.1% Tween 20 as detection antibody for 1 h on a microtiterplate shaker at room temperature. Unbound detection antibody is washed away three times with 300 µL/well PBST and the bound detection antibody is detected by addition of 100 µL ABTS/well. Determination of absorbance is performed on a Tecan Fluor Spectrometer at a measurement wavelength of 405 nm (reference wavelength 492 nm).

Ang-2 Binding BIACORE

Binding of the bispecific tetravalent antibodies to human Ang-2 is investigated by surface plasmon resonance using a BIACORE T100 instrument (GE Healthcare Biosciences AB, Uppsala, Sweden). Briefly, for affinity measurements goat<hIgG-Fcγ> polyclonal antibodies are immobilized on a CM5 chip via amine coupling for presentation of the bispecific tetravalent antibodies against human Ang-2. Binding is measured in HBS buffer (HBS-P (10 mM HEPES, 150 mM NaCl, 0.005% Tween 20, ph 7.4), 25° C. Purified Ang-2-His (R&D systems or in house purified) is added in various concentrations in solution. Association is measured by an Ang-2-injection of 3 minutes; dissociation is measured by washing the chip surface with HBS buffer for 3 minutes and a KD value is estimated using a 1:1 Langmuir binding model. Due to heterogenity of the Ang-2 preparation no 1:1 binding can be observed; KD values are thus only relative estimations. Negative control data (e.g. buffer curves) are subtracted from sample curves for correction of system intrinsic baseline drift and for noise signal reduction. Biacore T100 Evaluation Software version 1.1.1 is used for analysis of sensorgrams and for calculation of affinity data. Alternatively, Ang-2 could be captured with a capture level of 2000-1700 RU via a PentaHisAntibody (PentaHis-Ab BSA-free, Qiagen No. 34660) that is immobilized on a CM5 chip via amine coupling (BSA-free) (see below).

Ang-2-VEGF Bridging ELISA

Figure 7:
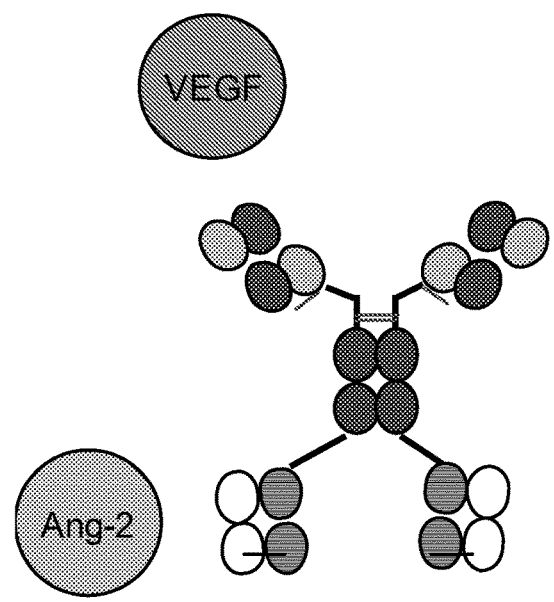
FIG. 7 Schematic structure of a bispecific antigen binding proteins according to the invention recognizing Ang-2 and VEGF (Example 3).

The binding properties of the bispecific tetravalent antibodies is evaluated in an ELISA assay with immobilized full-length VEGF165-His protein (R&D Systems) and human Ang-2-His protein (R&D Systems) for detection of bound bispecific antibody. Only a bispecific tetravalent <VEGF-Ang-2> antibody is able to o bind simultaneously to VEGF and Ang-2 and thus bridge the two antigens whereas monospecific "standard" IgG1 antibodies is not be capable of simultaneously binding to VEGF and Ang-2 (FIG. 7).

For this sake Falcon polystyrene clear enhanced microtiter plates are coated with 100 µl 2 µg/mL recombinant human VEGF 165 (R&D Systems) in PBS for 2 h at room temperature or over night at 4° C. The wells are washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series of purified bispecific tetravalent antibodies in PBS (Sigma) is added to the wells and incubated for 1 h on a microtiterplate shaker at room temperature. The wells are washed three times with 300 µl PBST (0.2% Tween 20) and bound antibody is detected by addition of 100 µl 0.5 µg/mL human Ang-2-His (R&D Systems) in PBS. The wells are washed three times with 300 µl PBST (0.2% Tween 20) and bound Ang-2 is detected with 100 µl 0.5 µg/mL <Ang-2>mIgG1-Biotin antibody (BAM0981, R&D Systems) for 1 h at room temperature. Unbound detection antibody is washed away with three times 300 µl PBST (0.2% Tween 20) and bound antibody is detected by addition of 100 µl 1:2000 Streptavidin-POD conjugate (Roche Diagnostics GmbH, Cat. No. 11089153) 1:4 diluted in blocking buffer for 1 h at room temperature. Unbound Streptavidin-POD conjugate is washed away with three-six times 300 µl PBST (0.2% Tween 20) and bound Strepatavidin-POD conjugate is detected by addition of 100 µL ABTS/well. Determination of absorbance is performed on a Tecan Fluor Spectrometer at a measurement wavelength of 405 nm (reference wavelength 492 nm).

Demonstration of Simultaneous Binding of Bispecific Tetravalent Antibody <VEGF-Ang-2> to VEGF-A and Ang-2 by Biacore In order to further corroborate the data from the bridging ELISA an additional assay is established to confirm simultaneous binding to VEGF and Ang-2 using surface plasmon resonance technology on a Biacore T100 instrument according to the following protocol and analyzed using the T100 software package (T100 Control, Version 2.01, T100 Evaluation, Version 2.01, T100 Kinetics Summary, Version 1.01): Ang-2 is captured with a capture level of 2000-1700 RU in PBS, 0.005% (v/v) Tween20 running buffer via a Penta-HisAntibody (PentaHis-Ab BSA-free, Qiagen No. 34660) that is immobilized on a CM5 chip via amine coupling (BSA-free). HBS-N buffer served as running buffer during coupling, activation is done by mixture of EDC/NHS. The PentaHis-Ab BSA-free Capture-Antibody is diluted in coupling buffer NaAc, pH 4.5, c=30 µg/mL, finally still activated carboxyl groups are blocked by injection of 1 M Ethanolamine; ligand densities of 5000 and 17000 RU are tested. Ang-2 with a concentration of 500 nM is captured by the PentaHis-Ab at a flow of 5 µL/min diluted with running buffer+1 mg/mL BSA. Subsequently, <Ang-2, VEGF> bispecific tetravalent antibody binding to Ang-2 and to VEGF is demonstrated by incubation with rhVEGF and formation of a sandwich complex. For this sake, the bispecific tetravalent <VEGF-Ang-2> antibody is bound to Ang-2 at a flow of 50 µL/min and a concentration of 100 nM, diluted with running buffer+1 mg/mL BSA and simultaneous binding is detected by incubation with VEGF (rhVEGF, R&D-Systems Cat.-No, 293-VE) in PBS+0.005% (v/v) Tween20 running buffer at a flow of 50 µL/min and a VEGF concentration of 150 nM. Association time 120 sec, dissociation time 1200 sec. Regeneration is done after each cycle at a flow of 50 μL/min with 2×10 mM Glycin pH 2.0 and a contact time of 60 sec. Sensorgrams are corrected using the usual double referencing (control reference: binding of bispecific antibody and rhVEGF to capture molecule PentaHisAb). Blanks for each Ab are measured with rhVEGF concentration "0".

Generation of HEK293-Tie2 Cell Line

In order to determine the interference of <Ang-2, VEGF> bispecific tetravalent antibodies with Ang-2 stimulated Tie2 phosphorylation and binding of Ang-2 to Tie2 on cells a recombinant HEK293-Tie cell line was generated. Briefly, a pcDNA3 based plasmid (RB22-pcDNA3 Topo hTie2) coding for full-length human Tie2 under control of a CMV promoter and a Neomycin resistance marker was transfected using Fugene (Roche Applied Science) as transfection reagent into HEK293 cells (ATCC) and resistant cells were selected in DMEM 10% FCS, 500 μg/mL G418. Individual clones were isolated via a cloning cylinder, and subsequently analyzed for Tie2 expression by FACS. Clone 22 was identified as clone with high and stable Tie2 expression even in the absence of G418 (HEK293-Tie2 clone22). HEK293-Tie2 clone22 is subsequently used for cellular assays: Ang-2 induced Tie2 phosphorylation and Ang-2 cellular ligand binding assay.

Ang-2 Induced Tie2 Phosphorylation Assay

Inhibition of Ang-2 induced Tie2 phosphorylation by <Ang-2, VEGF> bispecific tetravalent antibodies is measured according to the following assay principle. HEK293-Tie2 clone22 is stimulated with Ang-2 for 5 minutes in the absence or presence of Ang-2 antibody and P-Tie2 is quantified by a sandwich ELISA. Briefly, 2×10⁵ HEK293-Tie2 clone 22 cells per well are grown over night on a Poly-D-Lysine coated 96 well-microtiter plate in 100 μl DMEM, 10% FCS, 500 μg/mL Geneticin. The next day a titration row of <Ang-2, VEGF> bispecific tetravalent antibodies is prepared in a microtiter plate (4-fold concentrated, 75 μl final volume/well, duplicates) and mixed with 75 μl of an Ang-2 (R&D systems #623-AN] dilution (3.2 μg/mL as 4-fold concentrated solution). Antibodies and Ang-2 are pre-incubated for 15 min at room temperature. 100 μl of the mix are added to the HEK293-Tie2 clone 22 cells (pre-incubated for 5 min with 1 mM NaV3O4, Sigma #S6508) and incubated for 5 min at 37° C. Subsequently, cells are washed with 200 μl ice-cold PBS+1 mM NaV3O4 per well and lysed by addition of 120 μl lysis buffer (20 mM Tris, pH 8.0, 137 mM NaCl, 1% NP-40, 10% glycerol, 2 mM EDTA, 1 mM NaV3O4, 1 mM PMSF and 10 μg/mL Aprotinin) per well on ice. Cells are lysed for 30 min at 4° C. on a microtiter plate shaker and 100 μl lysate are transferred directly into a p-Tie2 ELISA microtiter plate (R&D Systems, R&D #DY990) without previous centrifugation and without total protein determination. P-Tie2 amounts are quantified according to the manufacturer's instructions and IC50 values for inhibition are determined using XLfit4 analysis plug-in for Excel (Dose-response one site, model 205). IC50 values can be compared within on experiment but might vary from experiment to experiment.

VEGF Induced HUVEC Proliferation Assay

VEGF induced HUVEC (Human Umbilical Vein Endothelial Cells, Promocell #C-12200) proliferation is chosen to measure the cellular function of <Ang-2, VEGF> bispecific tetravalent antibodies. Briefly, 5000 HUVEC cells (low passage number, <5 passages) per 96 well are incubated in 100 μl starvation medium (EBM-2 Endothelial basal medium 2, Promocell # C-22211, 0.5% FCS, Penicilline/Streptomycine) in a collagen I-coated BD Biocoat Collagen I 96-well microtiter plate (BD #354407/35640 over night. Varying concentrations of <Ang-2, VEGF> bispecific tetravalent antibody are mixed with rhVEGF (30 ngl/mL final concentration, BD #354107) and pre-incubated for 15 minutes at room temperature. Subsequently, the mix is added to the HUVEC cells and they are incubated for 72 h at 37° C., 5% CO2. On the day of analysis the plate is equilibrated to room temperature for 30 min and cell viability/proliferation is determined using the CellTiter-Glo™ Luminescent Cell Viability Assay kit according to the manual (Promega, # G7571/2/3). Luminescence is determined in a spectrophotometer.

Example 1

Figure 5:
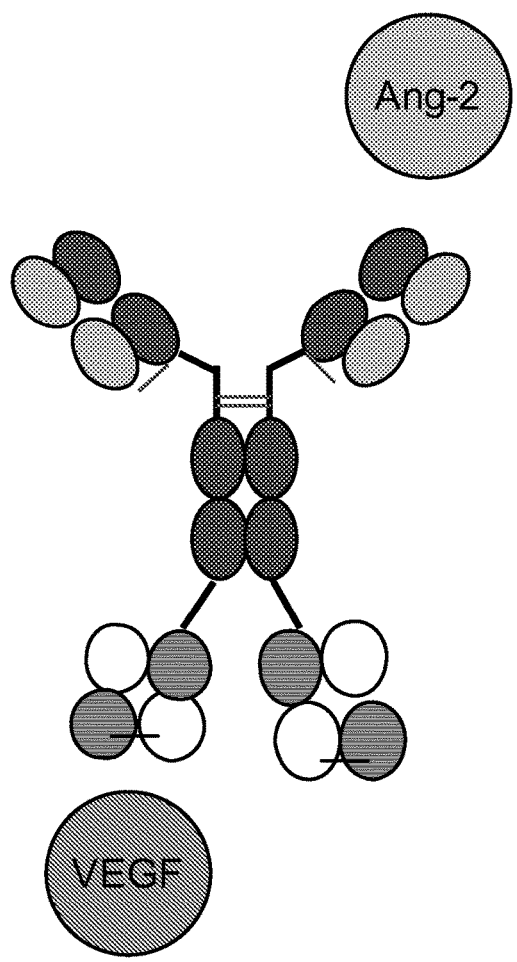
FIG. 5 Schematic structure of a bispecific antigen binding proteins according to the invention recognizing Ang-2 and VEGF (Example 1).

Production, Expression, Purification and Characterization of a Bispecific and Tetravalent Antibody Recognizing Ang-2 and VEGF-A In a first example a bispecific tetravalent antibody without a linker between the respective antibody chains recognizing Ang-2 and VEGF-A was made by fusing via a (G4S)4-connector a VH-CL domain fusion against VEGF-A to the C-terminus of the heavy chain of an antibody recognizing Ang-2 (SEQ1 or a corresponding IgG1 allotype). In order to obtain the bispecific tetravalent antibody this heavy chain construct was co-expressed with plasmids coding for the respective light chain of the Ang-2 antibody (SEQ3) and a VL-CH1 domain fusion recognizing VEGF-A (SEQ2). The scheme of the respective antibody is given in FIG. 5.

The bispecific tetravalent antibody is generated was described in the general methods section by classical molecular biology techniques and is expressed transiently in HEK293F cells as described above. Subsequently, it was purified from the supernatant by a combination of Protein A affinity chromatography and size exclusion chromatography. The obtained product was characterized for identity by mass spectrometry and analytical properties such as purity by SDS-PAGE, monomer content and stability.

| expression | purification | |
|---|---|---|
| Titer [μg/mL] | yield final product | homogeneity (final product) |
| 21 | 19.2 mg/L | 95% |

These data show that the bispecific tetravalent antibody can be produced in good yields and is stable.

Subsequently binding to Ang-2 and VEGF-A as well as simultaneous binding were studied by ELISA and Biacore assays described above and functional properties such as inhibition of Tie2 phosphorylation and inhibition of VEGF induced HUVEC proliferation are analyzed showing that the generated bispecific tetravalent antibody is able to bind to Ang-2 and VEGF-A and block their activity simultaneously.

Example 2

Figure 6:
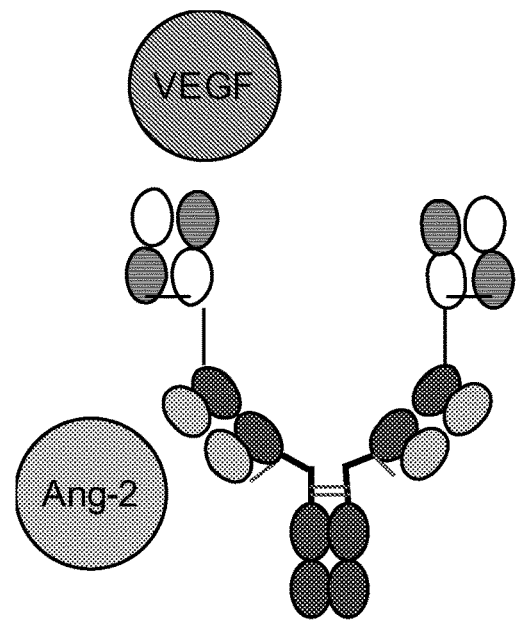
FIG. 6 Schematic structure of a bispecific antigen binding proteins according to the invention recognizing Ang-2 and VEGF (Example 2).

Production, Expression, Purification and Characterization of a Bispecific and Tetravalent Antibody Recognizing Ang-2 and VEGF-A In a second example a bispecific tetravalent antibody without a linker between the respective antibody chains recognizing Ang-2 and VEGF-A was made by fusing via a (G4S)4-connector a VH-CL domain fusion against VEGF-A to the N-terminus of the heavy chain of an antibody recognizing Ang-2 (SEQ4 or a corresponding IgG1 allotype). In order to obtain the bispecific tetravalent antibody this heavy chain construct was co-expressed with plasmids coding for the respective light chain of the Ang-2 antibody (SEQ3) and a VL-CH1 domain fusion recognizing VEGF-A (SEQ2). The scheme of the respective antibody is given in FIG. 6.

The bispecific tetravalent antibody was generated as described in the general methods section by classical molecular biology techniques and is expressed transiently in HEK293F cells as described above. Subsequently, it was purified from the supernatant by a combination of Protein A affinity chromatography and size exclusion chromatography. The obtained product was characterized for identity by mass spectrometry and analytical properties such as purity by SDS-PAGE, monomer content and stability.

| expression | purification | |
|---|---|---|
| Titer [µg/mL] | yield final product | homogeneity (final product) |
| 18 | 12.4 mg/L | 95% |

These data show that the bispecific tetravalent antibody can be produced in good yields and is stable.

Subsequently binding to Ang-2 and VEGF-A as well as simultaneous binding were studied by ELISA and Biacore assays described above and functional properties such as inhibition of Tie2 phosphorylation and inhibition of VEGF induced HUVEC proliferation are analyzed showing that the generated bispecific tetravalent antibody is able to bind to Ang-2 and VEGF-A and block their activity simultaneously.

Example 3

Production, Expression, Purification and Characterization of a Bispecific and Tetravalent Antibody Recognizing Ang-2 and VEGF-A In a third example a bispecific tetravalent antibody without a linker between the respective antibody chains recognizing Ang-2 and VEGF-A was made by fusing via a (G4S)4-connector a VH-CH1 Fab domain against Ang-2 to the C-terminus of the heavy chain of a CH1-CL exchange antibody recognizing VEGF (SEQ5 or a corresponding IgG1 allotype). In order to obtain the bispecific tetravalent antibody this heavy chain construct was co-expressed with plasmids coding for the respective light chain of the Ang-2 antibody (SEQ3) and a VL-CH1 domain fusion recognizing VEGF-A (SEQ2). The scheme of the respective antibody is given in FIG. 7.

The bispecific tetravalent antibody was generated as described in the general methods section by classical molecular biology techniques and is expressed transiently in HEK293F cells as described above. Subsequently, it was purified from the supernatant by a combination of Protein A affinity chromatography and size exclusion chromatography. The obtained product was characterized for identity by mass spectrometry and analytical properties such as purity by SDS-PAGE, monomer content and stability.

| expression | purification | |
|---|---|---|
| Titer [µg/mL] | yield final product | homogeneity (final product) |
| 8.5-9 | 1.8-4.1 mg/L | 100% |

These data show that the bispecific tetravalent antibody can be produced in good yields and is stable.

Subsequently binding to Ang-2 and VEGF-A as well as simultaneous binding were studied by ELISA and Biacore assays described above and functional properties such as inhibition of Tie2 phosphorylation and inhibition of VEGF induced HUVEC proliferation are analyzed showing that the generated bispecific tetravalent antibody is able to bind to Ang-2 and VEGF-A and block their activity simultaneously.

What is claimed is:

1. A bispecific antigen binding protein, comprising:
   a) two light chains and two heavy chains of an antibody that comprises two Fab fragments and that specifically binds to a first antigen; and
   b) two additional Fab fragments of an antibody which specifically binds to a second antigen, wherein the additional Fab fragments are both fused via a peptide connector either at the C- or N-termini of the heavy chains of a);
   wherein the bispecific antigen binding protein also comprises a structural modification selected from the group consisting of:
   i) in both Fab fragments of a) or in both Fab fragments of b)
      the variable domains VL and VH are replaced by each other, and the constant domains CL and CH1 are replaced by each other, or the constant domains CL and CH1 are replaced by each other;
   ii) in both Fab fragments of a)
      the variable domains VL and VH are replaced by each other, and
      the constant domains CL and CH1 are replaced by each other, and in both Fab fragments of b)
      the variable domains VL and VH are replaced by each other, or
      the constant domains CL and CH1 are replaced by each other;
   iii) in both Fab fragments of a)
      the variable domains VL and VH are replaced by each other, or
      the constant domains CL and CH1 are replaced by each other, and in both Fab fragments of b)
      the variable domains VL and VH are replaced by each other, and
      the constant domains CL and CH1 are replaced by each other;
   iv) in both Fab fragments of a)
      the variable domains VL and VH are replaced by each other, and
      in both Fab fragments of b)
      the constant domains CL and CH1 are replaced by each other; and
   v) in both Fab fragments of a)
      the constant domains CL and CH1 are replaced by each other, and in both Fab fragments of b)
      the variable domains VL and VH are replaced by each other.

2. The bispecific antigen binding protein according to claim 1
   wherein said additional Fab fragments are both fused via a peptide connector either to the C-termini of the heavy chains of a), or to the N-termini of the heavy chains of a).

3. The bispecific antigen binding protein according to claim 1, wherein the Fab fragments comprise the following structural modifications:
   i) in both Fab fragments of a), or in both Fab fragments of b),
      the variable domains VL and VH are replaced by each other and the constant domains CL and CH1 are replaced by each other, or the constant domains CL and CH1 are replaced by each other.

4. The bispecific antigen binding protein according to claim 3, wherein the Fab fragments comprise the following structural modifications:

i) in both Fab fragments of a)

the variable domains VL and VH are replaced by each other and the constant domains CL and CH1 are replaced by each other, or the constant domains CL and CH1 are replaced by each other.

5. The bispecific antigen binding protein according to claim 4, wherein the Fab fragments comprise the following structural modifications:

i) in both Fab fragments of a)

the constant domains CL and CH1 are replaced by each other.

6. The bispecific antigen binding protein according to claim 3, wherein the Fab fragments comprise the following structural modifications:

i) in both Fab fragments of b)

the variable domains VL and VH are replaced by each other and the constant domains CL and CH1 are replaced by each other, or the constant domains CL and CH1 are replaced by each other.

7. The bispecific antigen binding protein according to claim 6, the Fab fragments comprise the following structural modifications:

i) in both Fab fragments of b)

the constant domains CL and CH1 are replaced by each other.

8. A pharmaceutical composition comprising the bispecific antigen binding protein according to claim 1 and at least one pharmaceutically acceptable excipient.

* * * * *